US006737245B1

(12) United States Patent
Francis et al.

(10) Patent No.: US 6,737,245 B1
(45) Date of Patent: May 18, 2004

(54) LUCIFERASE EXPRESSION CASSETTES AND METHODS OF USE

(75) Inventors: Kevin P. Francis, Alameda, CA (US); Pamela R. Contag, San Jose, CA (US); Danny J. Joh, Fremont, CA (US)

(73) Assignee: Xenogen Corporation, Alameda, CA (US)

( * ) Notice: Subject to any disclaimer, the term of this patent is extended or adjusted under 35 U.S.C. 154(b) by 0 days.

(21) Appl. No.: 09/657,289

(22) Filed: Sep. 7, 2000

Related U.S. Application Data
(60) Provisional application No. 60/152,904, filed on Sep. 8, 1999.

(51) Int. Cl.$^7$ .............................. C12N 9/02; C12N 1/19; C12N 15/52; G01N 33/52; C07H 21/04
(52) U.S. Cl. ................. 435/8; 435/189; 435/252.3; 435/252.31; 435/253.4; 435/253.5; 435/320.1; 436/2; 536/23.2; 536/24.1
(58) Field of Search .................... 435/189, 320.1, 435/252.3, 252.31, 253.4, 253.5, 8; 436/2; 536/23.2, 24.1

(56) References Cited

U.S. PATENT DOCUMENTS

| | | | | |
|---|---|---|---|---|
| 5,221,623 A | * | 6/1993 | Legocki et al. | 435/252.3 |
| 5,650,135 A | | 7/1997 | Contag et al. | 424/9.1 |
| 5,670,356 A | * | 9/1997 | Sherf et al. | 435/189 |
| 5,900,362 A | | 5/1999 | Eberz et al. | 435/37 |
| 6,020,121 A | | 2/2000 | Bao et al. | 435/4 |
| 6,217,847 B1 | | 4/2001 | Contag et al. | 424/9.1 |

FOREIGN PATENT DOCUMENTS

| | | |
|---|---|---|
| EP | 1 016419 A2 | 7/2000 |
| FR | 2 693 475 | 1/1994 |
| WO | WO 90/04041 | 4/1990 |
| WO | WO 93/16172 | 8/1993 |
| WO | WO 96/40979 A1 | 12/1996 |
| WO | WO 97/11690 A3 | 4/1997 |
| WO | WO 97/11690 A2 | 4/1997 |
| WO | WO 97/18841 | 5/1997 |
| WO | WO 97/40381 S1 | 10/1997 |
| WO | WO 99/14311 | 3/1999 |
| WO | WO 00/36106 | 6/2000 |
| WO | WO 01/18195 A2 | 3/2001 |
| WO | WO 01/18225 A1 | 3/2001 |
| WO | WO 01/37195 A2 | 5/2001 |

OTHER PUBLICATIONS

Vellanoweth et al. (1992) Mol. Microbiol, vol. 6(9), 1105–1114.*

Schauer. (1988) Trends Biotechnol., vol. 6, No. 1, pp. 23–27 (abstract).*

Bianchi et al., "Stress Responses as a Tool to Detect and Characterize the Mode of Action of Antibacterial Agents," *Applied and Environmental Microbiology* 65(11):5023–5027 (1999).

Francis et al., "Monitoring Bioluminiscent Staphylococcus Aureus Infections in Living Mice Using a Novel LuxAB-CDE Construct," *Infection and Immunity* 68(6):3594–3600 (2000).

Kozlowski et al., "Vectors Permitting Visual Monitoring of Simple Transposition Events," *Gene* 80(2):217–225 (1989).

Lingnau et al., "Expression of the Listeria Monocytogenes EGD inIA and inIB Genes, Whose Products Mediate Bacterial Entry into Tissue Culture Cell Lines, by PrfA–Dependent and –Independent Mechanisms," *Infection and Immunity* 63(10):3896–3903 (1995).

Loessner et al., "Structural Proteins and DNA Characteristics of 14 Listeria Typing Bacteriophases," *Journal of General Virology* 75:701–710 (1994).

Loessner and Scherer, "Organization and Transcriptional Analysis of the Listeria Phage A511 Late Gene Region Comprising the Major Capsid and Tail Sheath Protein Genes cps and tsh," *Journal of Bacteriology* 177(22):6601–6609 (1995).

Lunsford, Dwayne R., "A Tn4001 Delivery System for Streptococcus Gordonii, (Challis)" *Plasmid* 33(2):153–157 (1995).

Beyer and Böhm, "Labelling Salmonella Live Vaccine Strains with the lux Operon from Vibrio Fischeri Improves Their Detection and Discrimination from Wild Type," *Microbiol. Res.* 151:407–419 (1996).

Meighn, E. A., "Genetics of Bacterial Bioluminescence," *Annu. Rev. Genet.* 28:117–139 (1994).

Sohaskey et al., "Tn456 and Luciferase: Synergistic Tools for Visualizing Transcription in Streptomyces," *Gene* 115:67–71 (1992).

Hahn, T., et al., "Construction and Analysis of Modified Tn4001 Conferring Chloramphenicol Resistance in Mycoplasma Pneumoniae," *Plasmid* 41:120–124 (1999).

Jacobs et al., "Highly Bioluminescent *Bacillus Subtilis* Obtained Through High–level Expression of a luxAB Fusion Gene," *Mol. Gen. Genet* 230:251–256 (1991).

Phillips–Jones, M.K. "Bioluminescence (lux) Expression in the Anaerobe *Clostridium Perfringens,*" *FEMS Microbiology Letters* 106:265–270 (1993).

Loimaranta, et al., "Generation of Bioluminescent Steptococcus mutans and Its Usage in Rapid Analysis of the Efficacy of Antimicrobial Compounds" *Antimicrobial Agents and Chemotherapy* 42(8):1906–1910 (1998).

(List continued on next page.)

*Primary Examiner*—Elizabeth Slobodyansky
(74) *Attorney, Agent, or Firm*—Robins & Pasternak LLP

(57) ABSTRACT

The present invention relates to bacterial luciferase expression cassettes suitable for conferring bioluminescence properties on Gram-positive bacteria, cells transformed with such cassettes, and methods of making and using such cassettes.

37 Claims, 4 Drawing Sheets

OTHER PUBLICATIONS

Meighen, E.A., "Bacterial Bioluminescence: Organization, Regulation, and Application of the lux Genes," *FASEB Journal* 7(11):1016–1022 (1993).

O'Connell, K.P., et al., "Identification of Cold Shock Gene Loci in Sinorhizobium melilot by Using a luxAB Reporter Transposon," *Appl. Environ. Microbiol.* 66(1):401–405 (2000).

Roy, G., et al., "Episomal and Stable Expression of the Luciferase Reporter Gene for Quantifying Leishmania SPP. Infections in Macrophages and in Animal Models," *Molecular and Biochemical Parasitology* 110:195–206 (2000).

Sibakov, M., et al., "Secretion of TEM β–Lactamase with Signal Sequences Isolated from the Chromosome of *Lactococcus lactis* subsp. lactis," *Appl. Environ. Microbiology* 57(2):341–348 (1991).

Sohaskey et al., "Construction and Application of Plasmid–and Transposon–Based Promoter–Probe Vectors for Streptomyces ssp. That Employ a *Vibrio harveyi* Luciferase Reporter Cassette," *Journal of Bacteriology* 174(2):367–376 (1992).

Steidler, et al., "The Expression of *Photinus pyralis* Luciferase Gene in *Stephylococcus aureus* Cowan I allows the Development of a Live Amplifiable Tool for Immunodetection" Applied and Environmental Microbiology 62(7):2356–2359 (1996).

Steinmann, et al., "Saturation Mutagenesis in *Escherichia coli* of a Cloned *Xanthomonas campestris* DNA Fragment with the lux Transposon Tn4431 Using the Delivery Plasmid pDS1, Thermosensitive in Replication," *Appl. Microbiol. Biotechnol.* 40:356–360 (1993).

Ulitzur, S., J. "Established Technologies and New Approaches in Applying Luminous Bacteria for Analytical Purposes," Biolumin Chemilumin 12:179–92 (1997).

Zhang et al., "Bioluminescence for Biological Sensing in Living Mammals," *Oxygen Transport to Tissue XXI*, edited by Eke and Delpy. Kluwer Academic/Plenum Publishers, New York, (1999).

* cited by examiner

US 6,737,245 B1

LUCIFERASE EXPRESSION CASSETTES AND METHODS OF USE

This application claims the benefit of provisional application No. 60/152,904, filed Sep. 8, 1999.

TECHNICAL FIELD

The present invention relates to luciferase expression vectors, methods of making same and methods of use thereof.

BACKGROUND OF THE INVENTION

Bioluminescent bacteria are widely found in both marine and terrestrial environments. Interestingly, all identified species of naturally occurring marine and terrestrial bioluminescent bacteria are Gram-negative. To date, at least eleven species in four Gram-negative genera have been described: Vibrio, Photobacterium, Shewanella (Altermonas) and Photorhabdus (Xenorhabdus). In all these species, the five genes responsible for bioluminescence are clustered in the lux operon (luxCDABE).

The bioluminescence (emitted blue-green light having a wavelength of about 490 nm) is thought to result from a luciferase-catalyzed oxidation of reduced flavin mononucleotide ($FMNH_2$) and a long-chain fatty aldehyde. The luciferase enzyme is encoded by two subunits (luxAB), whereas the fatty acid reductase polypeptides responsible for the biosynthesis of the aldehyde substrate for the luminescent reaction are encoded by the three genes luxCDE. The genes encoding luciferase and the fatty acid reductase polypeptides have been cloned from the lux operons of Vibrio, Photobacterium and Photorhabdus and sequenced. In each case, the luxCDE genes flank the luxAB genes, with transcription in the order luxCDABE. Although a number of additional lux genes have been identified in each of these three bacteria, only luxAE are essential for the biosynthesis of light (reviewed by Meighen, E., (1993, *The FASEB Journal* 7:1016–1022 and Ulitzur, S., (1997), *J. Biolumin Chemilumin* 12:179–192).

Methods described in U.S. Pat. No. 5,650,135, make possible the detection of bioluminescent bacteria in a living animal without dissecting or otherwise opening the animal up ("in vivo monitoring")—the light is detected through muscle, skin, fur & other traditionally "opaque" tissues using a highly sensitive camera. In this context and others, it would therefore be desirable to confer bioluminescence properties on a bacterium of one's choice, so that the bacterium could be followed with in vivo monitoring in various models of infection. In particular, it would be desirable to confer such bioluminescence properties on Gram-positive bacteria, since many bacteria pathogenic to mammals are in fact Gram-positive. For example, infections caused by Stapholococcus, a Gram-positive cocci, are ubiquitous and include, e.g., abscesses, mastitis, pneumonia, bacteremia, osteomyletis, enterocolitis and toxic shock syndrome (TSS). Another Gram-positive cocci, Streptococcus is the primary cause of pharyngeal infections ("strep" throat). Gram-positive bacilli such as Anthrax and Listeria (which causes meningitis) can cause severe, and even fatal infections in humans and other mammals.

While a non-bioluminescent Gram-negative bacterium can typically be engineered to have bioluminescence properties by cloning into it a luxCDABE operon (under control of a suitable promoter) from a bioluminescent species (see, e.g., Contag, et al., U.S. Pat. No. 5,650,135), previous attempts to make bioluminescent Gram-positive bacteria have met with limited success. For example, one approach employed an expression cassette encoding a functional LuxAB fusion protein (Jacobs, M., et al., (1991) *Mol. Gen. Genet.* 230:251–256). In this cassette, a Gram-positive ribosome binding site (RBS) was inserted upstream of luxA, with the luxB gene cloned in frame downstream of luxA. Although this approach has been successful in generating a number of novel genera of bioluminescent Gram-positive bacteria useful for certain environmental and food safety studies (e.g., the assessment of food products for contamination by such bacteria), these bacteria are not useful for studying pathogenicity. A major reason for this limitation is that the LuxAB fusion proteins described in the prior art not stable at mammalian body temperatures, and are thus capable of catalyzing only minimal light production in bacterial cells at 37° C.

In fact, none of the bioluminescent Gram-positive bacteria which have been published to date produce enough light in vivo to make them useful for the in vivo monitoring applications discussed above. It would therefore be desirable to have a method by which Gram-positive bacteria could be made to bioluminescence at temperatures found in mammalian host cells, and at levels of brightness suitable for monitoring in living animals. The present invention provides, inter alia, such methods, expression cassettes, and other tools useful for generating bioluminescent Gram-positive bacteria suitable for studies relating to infection and/or pathogenesis.

SUMMARY OF THE INVENTION

In one aspect, the invention includes an expression cassette comprising a polynucleotide encoding luxA, luxB, luxC, luxD and luxE gene products, wherein (a) the arrangement of coding sequences for the gene products is in the following relative order 5'-luxA-luxB-luxC-luxD-luxE-3'; (b) transcription of the polynucleotide results in a polycistronic RNA encoding all the gene products; and (c) each of the luxA, luxB, luxC, luxD and luxE gene products is expressed as an individual polypeptide. In one embodiment, the expression cassette includes a multiple-insertion site located adjacent the 5' end of the luxA coding sequences. In another embodiment, the expression cassette further comprises at least one Gram-positive ribosome binding site sequence (SEQ ID NO:1) upstream of each of the polynucleotide sequences encoding each of the luxA, luxB, luxC, luxD and luxE gene products. The coding sequences of the gene products preferably encode a luciferase that is stable at 37° C., such as the luciferase of *Photorhabdus luminescens*. Accordingly, the nucleotide coding sequences for the luciferase are preferably derived from such organisms. In one series of embodiments, transcription of the polynucleotide is mediated by a promoter contained in an Expression Enhancing Sequence selected from the group consisting of Sa1–Sa6; such as Sa2 or Sa4. In a related series of embodiments, transcription of the polynucleotide is mediated by a promoter contained in an Expression Enhancing Sequence selected from the group consisting of Sp1, Sp5, Sp6, Sp9, Sp16 and Sp17 (e.g., Sp16).

In another aspect, the invention includes an expression cassette comprising a polynucleotide encoding luxA, and luxB gene products, wherein (a) transcription of the polynucleotide results in a polycistronic RNA encoding both gene products, and (b) polynucleotide sequences comprising Gram-positive ribosome-binding site sequences are located adjacent the 5' end of the luxA coding sequences and adjacent the 5' end of the luxB coding sequences. In one embodiment, the expression cassette further comprises an insertion site 5' to at least one of either the luxA or luxB coding sequences. The insertion site may, for example, further comprise a multiple-insertion site. In one embodiment, the multiple-insertion site is located 5' to the luxA coding sequences. In a related embodiment, the multiple-insertion site is located 5' to the luxB coding sequences. In another embodiment, the polynucleotide further encodes luxC, luxD and luxE gene products. The arrangement of the coding sequences for the lux gene products may be, for example, in the following relative order 5'-luxA-luxB-luxC-luxD-luxE-3'. Preferably, Gram-positive bacterial Shine-Dalgarno sequences are 5' to all of the lux coding sequences. In one group of embodiments, transcription of the polynucleotide is mediated by a promoter contained in an Expression Enhancing Sequence selected from the group consisting of Sa1–Sa6, e.g., Sa2 or Sa4. In another group of embodiments, transcription of the polynucleotide is mediated by a promoter contained in an Expression Enhancing Sequence selected from the group consisting of Sp1, Sp5, Sp6, Sp9, Sp16 and Sp17, such as Sp16. As was described above, the coding sequences for luxA and luxB are preferably obtained from an organism with a luciferase that is stable at 37° C., such as *Photorhadus luminescens*.

In yet another aspect, the invention includes an expression cassette comprising a polynucleotide encoding luxA, luxB, and luc gene products, wherein (a) transcription of the polynucleotide results in a polycistronic RNA encoding all three gene products, and (b) polynucleotide sequences comprising Gram-positive bacterial Shine-Dalgarno sequences are located adjacent the 5' end of the luxA coding sequences, adjacent the 5' end of the luxB coding sequences, and adjacent the 5' end of the luc coding sequences. In one embodiment, the polynucleotide further encodes luxC, luxD and luxE gene products. In another embodiment, Gram-positive bacterial Shine-Dalgarno sequences are located 5' to all of the lux coding sequences or 5' to luxA and luxC only. In one set of embodiments, transcription of the polynucleotide is mediated by a promoter contained in an Expression Enhancing Sequence selected from the group consisting of Sa1–Sa6, e.g., Sa2 or Sa4. In a related set, transcription of the polynucleotide is mediated by a promoter contained in an Expression Enhancing Sequence selected from the group consisting of Sp1, Sp5, Sp6, Sp9, Sp16 and Sp17, e.g., Sp16. The expression cassette may further include a multiple-insertion site located adjacent the 5' end of the luxA coding sequences. In a preferred embodiment, the coding sequences for luxA and luxB are obtained from *Photorhadus luminescens*.

Also included in the invention is an expression cassette comprising a polynucleotide encoding an in-frame fusion of luxA and luxB gene products, wherein (a) polynucleotide sequences comprising Gram-positive Shine-Dalgarno sequences are located adjacent the 5' end of the luxA coding sequences, and (b) an insertion site is located between the luxA and luxB coding sequences. The insertion site may further comprise a multiple-insertion site. In one embodiment, the polynucleotide further encodes luxC, luxD and luxE gene products. Arrangement of coding sequences for the gene products is preferably, but not necessarily, in the following relative order 5'-luxA-luxB-luxC-luxD-luxE-3'. In a preferred embodiment, Gram-positive bacterial Shine-Dalgarno sequences are 5' to the luxA-luxB fusion coding sequences and all of the luxC, luxD, and luxE coding sequences.

It will be appreciated that all of the expression cassettes described above may be contained within a bacterial transposon or bacterial mini-transposon. Further, in all these cassettes, the coding sequences of the gene products may comprise codons that are optimal for expression of the gene products in a host system into which the expression cassette is to be introduced.

Also included in the invention is a method of selecting a light-producing expression cassette for use in a selected cell type. The method includes the steps of (i) preparing fragments of genomic DNA isolated from the selected cell type, and (ii) inserting the fragments into the insertion site of an expression cassette comprising, a polynucleotide encoding an in-frame fusion of luxA and luxB gene products, wherein (a) polynucleotide sequences comprising Gram-positive Shine-Dalgarno sequences are located adjacent the 5' end of the luxA coding sequences, and (b) an insertion site is located between the luxA and luxB coding sequences. The expression cassette is preferably capable of expressing the gene products in the selected cell type. Step (iii) of the method is introducing the expression cassettes carrying the fragments into cells of the selected cell type, and step (iv) is screening for cells producing light, where the light production is mediated by the expression cassette. The fragments may be produced, for example, by enzymatic digestion of genomic DNA, partial digestion using a selected restriction endonuclease, or by mechanical fragmentation of genomic DNA. Transcription of the lux genes is preferably mediated by a promoter that is obtained from the selected cell type, for example, Staphylococcus, Streptococcus, Actinomyces, Lactobacillus, Corynebacterium, Mycobacterium, Clostridium, Propionibacterium, Enterococcus, or Bacillus. In one embodiment, the screening is carried out at a temperature greater than about 37° C.

The invention further includes a luciferase expression cassette comprising: a) a polynucleotide encoding luc; and b) polynucleotide sequences comprising expression enhancing sequences (e.g., Gram-positive promoter and/or Gram-positive Shine-Dalgarno sequences) obtained from Gram-positive bacteria 5' to the luc-encoding polynucleotide. The small DNA fragment comprising expression enhancing sequences is preferably between luc and the promoter.

The invention further includes a luciferase expression cassette comprising: a) a polynucleotide encoding luxY; and b) polynucleotide sequences comprising expression enhancing sequences (e.g., Gram-positive promoter and/or Gram-positive Shine-Dalgarno sequences) obtained from Gram-positive bacteria 5' to the luxY-encoding polynucleotide. The small DNA fragment comprising expression enhancing sequences is preferably between luxY and the promoter.

Also included in the invention are the plasmids designated as pCMOR G+1 Sa1–6 and pCMOR G+2 Sp1, Sp5, Sp6, Sp9, Sp16 and Sp17.

In another aspect, the invention includes a shuttle vector comprising a) an expression cassette according to any of the expression cassettes described above; b) a polynucleotide encoding a selectable marker, c) a Gram-positive origin of replication; and d) a Gram-negative origin of replication.

Yet another aspect of the invention encompasses a method of screening for expression enhancing sequences that are useful in obtaining expression of luciferase in Gram-positive bacteria. The method comprises the steps of a) introducing DNA fragments from a Gram-positive bacterial genome into an expression cassette comprising (i) polynucleotides encoding luxA, luxB, luxC, luxD and luxE gene products, where the polynucleotides are in the following relative order 5'-luxABCDE; (ii) polynucleotide sequences comprising expression enhancing sequences obtained from Gram-positive bacteria 5' to at least one of the lux-encoding polynucleotides and (iii) an insertion site 5' to at least one of the lux-encoding polynucleotides; b) transforming the expression cassette of step (a) into a Gram-positive bacteria host cells; and c) determining the level of luciferase activity in the host cell, thereby identifying Gram-positive expression enhancing DNA sequences that are useful in obtaining expression of luciferase in Gram-positive bacteria.

Still another aspect of the invention includes a method of screening for expression enhancing sequences that are useful in obtaining expression of luciferase in Gram-positive bacteria. The method includes the steps of a) introducing DNA fragments from a Gram-positive bacterial genome into an expression cassette comprising (i) polynucleotides encoding luxA, luxB gene products (ii) polynucleotide sequences comprising expression enhancing sequences obtained from Gram-positive bacteria 5' to at least one of the lux-encoding polynucleotides and (iii) an insertion site 5' to at least one of the lux-encoding polynucleotides; b) transforming the expression cassette of step (a) into a Gram-positive bacteria host cells; and c) determining the level of luciferase activity in the host cell, thereby identifying Gram-positive expression enhancing DNA sequences that are useful in obtaining expression of luciferase in Gram-positive bacteria.

Also part of the invention is a method of screening for expression enhancing sequences that are useful in obtaining expression of luciferase in Gram-positive bacteria. The method comprises the steps of: a) introducing DNA fragments from a Gram-positive bacterial genome into an expression cassette comprising (i) a polynucleotide encoding luc; (ii) polynucleotide sequences comprising expression enhancing sequences obtained from Gram-positive bacteria 5' to the luc-encoding polynucleotide and (iii) an insertion site 5' to at least one of the luc-encoding polynucleotide; b) transforming the expression cassette of step (a) into a Gram-positive bacteria host cells; and c) determining the level of luciferase activity in the host cell, thereby identifying Gram-positive expression enhancing DNA sequences that are useful in obtaining expression of luciferase in Gram-positive bacteria.

In another aspect, the invention includes a method of making a luciferase expression cassette, comprising the steps of: (a) preparing polynucleotides encoding in a 5'-3' direction luxA, luxB, luC, luxD and luxE gene products; and Gram-positive Shine-Dalgarno nucleotide sequences operably linked to one or more of the lux-encoding polynucleotides; and (b) inserting small sequences of nucleic acids between one or more of the polynucleotides encoding a lux gene product.

The present invention includes a method of making a luciferase expression cassette, comprising the steps of: (a) preparing polynucleotides encoding luxA and luxB gene products; and Gram-positive Shine-Dalgarno nucleotide sequences operably linked to one or more of the lux-encoding polynucleotides; and (b) inserting small sequences of nucleic acids between one or more of the polynucleotides encoding a lux gene product.

The invention also includes a method of making a luciferase expression cassette, comprising the steps of: (a) preparing polynucleotides encoding luc gene product; and Gram-positive Shine-Dalgarno nucleotide sequences operably linked to the luc-encoding polynucleotide; and (b) inserting small sequences of nucleic acids 5' to the luc-encoding polynucleotide.

The invention also includes a method of making a luciferase expression cassette, comprising the steps of: (a) preparing polynucleotides encoding luxY gene product; and Gram-positive Shine-Dalgarno nucleotide sequences operably linked to the luxY-encoding polynucleotide; and (b) inserting small sequences of nucleic acids 5' to the luxY-encoding polynucleotide.

Also part of the invention is a method of modifying a Gram-positive organism to produce light, comprising transforming the Gram-positive organism with any of the expression cassettes described above.

In another aspect, the invention includes a method of screening an analyte for its ability to affect expression of a reporter marker, comprising: (a) transforming Gram-positive bacteria with any of the luciferase expression cassettes described above; (b) providing the analyte to the bacteria; (c) providing, if necessary, the substrate required for luciferase light production; and (d) monitoring the effect of the analyte on the ability of the Gram-positive bacteria to produce light, thereby identifying whether the analyte affects expression of the reporter in Gram-positive bacteria. In one embodiment, the substrate is aldehyde and is provided as a vapor.

Also included in the invention is a method of screening an analyte for its ability to affect expression of a reporter marker in a whole animal. The method includes the steps of (a) transforming Gram-positive bacteria with any of the luciferase expression cassettes described above; (b) introducing the bacteria into a whole animal; (c) providing the analyte to the animal; (d) providing, if necessary, the substrate required for luciferase light production; and (e) monitoring the effect of the analyte on the ability of the Gram-positive bacteria to produce light, thereby identifying whether the analyte affects expression of the reporter in Gram-positive bacteria. In one embodiment, the substrate is aldehyde and is provided by injection.

In another aspect, the invention includes Gram-positive bacteria capable of producing light, wherein (a) the bacteria comprise lux and luxB coding sequences, and (b) about $1 \times 10^6$ bacterial cells can produce at least about $1 \times 10^4$ Relative Light Units at about 37° C. In other embodiments, cells emitting at least about 10 photons per second per cell are disclosed. Cells emitting at least about 25 photons per second per cell are also included. Cells emitting at least about 50 photons per second per cell are disclosed. Cells emitting at least about 75 photons per second per cell are disclosed. Cells emitting at least about 100 photons are also disclosed.

In yet another aspect, the invention includes a transgenic non-human animal comprising any of the expression cassettes described above.

Also included in the invention is a promoter sequences contained in any of Expression-enhancing sequences Sa1–Sa6 or Sp sequences (as disclosed below). In a preferred embodiment, the promoter sequence is selected from Expression-Enhancing Sequences selected from the group consisting of SEQ ID NOS:15–26.

In a general embodiment, the invention includes an expression cassette comprising a promoter sequence as defined in the above paragraph operably linked to a polynucleotide sequence encoding a light-generating protein (LGP). In one embodiment, the LGP is a fluorescent protein, such as green fluorescent protein. In another embodiment, the LGP is a luminescent or bioluminescent protein, such as luciferase. In specific embodiments, the luciferase may either a prokaryotic luciferase (a lux-encoded luciferase) or a eukaryotic (luc-encoded) luciferase.

In yet another aspect, the invention includes a method for localizing an entity in a non-human mammalian subject, comprising the following steps: (a) administering to the subject a conjugate of the entity and a prokaryotic luciferase comprising the alpha and beta subunits, (b) delivering aldehyde to the subject, (c) after a period of time in which the conjugate can achieve localization in the subject, measuring through opaque tissue, photon emission from the luciferase localized in the subject, with a photodetector device until an image of photon emission can be constructed, and (d) constructing an image of photon emission, wherein the image shows the localization of the entity in the mammalian subject.

The invention also includes bacterial host cells, for example gram-positive bacteria, comprising one or more the expression vectors, plasmids, transposons, etc described herein.

These and other embodiments of the present invention will readily occur to those of ordinary skill in the art in view of the disclosure herein. Furthermore, various forms of the different embodiments described herein may be combined.

DETAILED DESCRIPTION OF THE INVENTION

Figure 1:
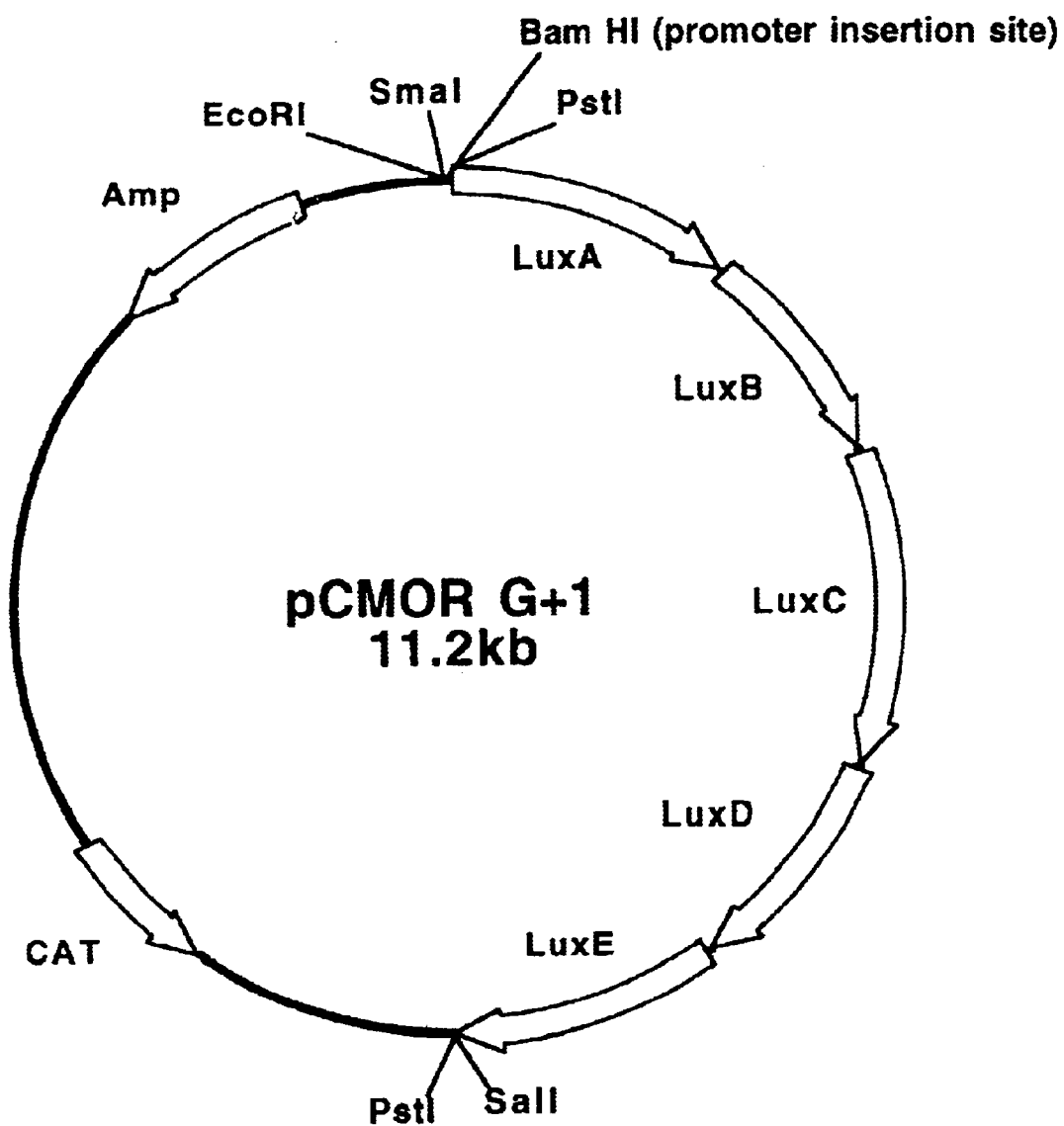
FIG. 1 is a schematic diagram of the plasmid pCMOR G+1. Plasmid backbone is pMK4 (9). Nucleotide sequences of the lux genes, ordered as shown, are as given in GenBank (accession number M90093) flanked by the relevant sequences shown in table 1. Plasmid can be used as a promoter-probe vehicle by ligating genomic DNA (partially digested by 4 base cutter) at the unique BamHI or SmaI sites and selecting for light in the Gram-positive bacterium from which the DNA was derived.

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I–IV (D. M. Weir and C. C. Blackwell, eds., 1986, Blackwell Scientific Publications); Ausubel, F. M., et al., *Current Protocols in Molecular Biology*, John Wiley and Sons, Inc., Media, Pa. (1995). Sambrook, J., et al., *Molecular Cloning: A Laboratory Manual*, Second Edition, Cold Spring Harbor Laboratory (Cold Spring Harbor, N.Y.) (1989)).

All publications, patents and patent applications cited herein, whether supra or infra, are hereby incorporated by reference in their entirety.

Definitions

In describing the present invention, the following terms will be employed, and are intended to be defined as indicated below. Unless otherwise indicated, all terms used herein have the same meaning as they would to one skilled in the art of the present invention.

As used in this specification and the appended claims, the singular forms "a," "an" and "the" include plural references unless the content clearly dictates otherwise. Thus, for example, reference to "an antigen" includes a mixture of two or more such agents.

The terms "nucleic acid molecule" and "polynucleotide" are used interchangeably to and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term polynucleotide sequence is the alphabetical representation of a polynucleotide molecule. This alphabetical representation can be input into databases in a computer having a central processing unit and used for bioinformatics applications such as functional genomics and homology searching.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription regulators, such as promoters, transcription enhancer elements, transcription termination signals, and polyadenylation sequences; and translation regulators, such as sequences for optimization of initiation of translation, e.g., Shine-Dalgarno (ribosome binding site) sequences, and translation termination sequences. Promoters can include inducible promoters (where expression of a polynucleotide sequence operably linked to the promoter is induced by an analyte, cofactor, regulatory protein, etc.), repressible promoters (where expression of a polynucleotide sequence operably linked to the promoter is induced by an analyte, cofactor, regulatory protein, etc.), and constitutive promoters.

"Expression enhancing sequences" typically refer to control elements that improve transcription or translation of a polynucleotide relative to the expression level in the absence of such control elements (for example, promotors, promoter enhancers, enhancer elements, and translational enhancers (e.g., Shine-Dalgarno sequences)).

An "isolated polynucleotide" molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is typically called a polypeptide or a protein.

"Operably linked" refers to an arrangement of elements wherein the components so described are configured so as to perform their usual function. Thus, a given promoter that is operably linked to a coding sequence (e.g., a reporter gene) is capable of effecting the expression of the coding sequence when the proper enzymes are present. The promoter or other control elements need not be contiguous with the coding sequence, so long as they function to direct the expression thereof. For example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transformed. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining nucleic acid and amino acid "sequence identity" also are known in the art. Typically, such techniques include determining the nucleotide sequence of the mRNA for a gene and/or determining the amino acid sequence encoded thereby, and comparing these sequences to a second nucleotide or amino acid sequence. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482–489 (1981). This algorithm can be applied to amino acid sequences by using the scoring matrix developed by Dayhoff, *Atlas of Protein Sequences and Structure*, M. O. Dayhoff ed., 5 suppl. 3:353–358, National Biomedical Research Foundation, Washington, D.C., USA, and normalized by Gribskov, *Nucl. Acids Res.* 14(6):6745–6763 (1986). An exemplary implementation of this algorithm to determine percent identity of a sequence is provided by the Genetics Computer Group (Madison, Wis.) in the "BestFit" utility application. The default parameters for this method are described in the *Wisconsin Sequence Analysis Package Program Manual*, Version 8 (1995) (available from Genetics Computer Group, Madison, Wis.). A preferred method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: www.ncbi.nlm.gov/cgi-bin/ BLAST.

Alternatively, homology can be determined by hybridization of polynucleotides under conditions which form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%–85%, preferably at least about 90%, and most preferably at least about 95%–98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

A "gene" refers to a polynucleotide containing at least one open reading frame that is capable of encoding a particular polypeptide or protein after being transcribed or translated. Any of the polynucleotide sequences described herein may be used to identify larger fragments or full-length coding sequences of the genes with which they are associated. Methods of isolating larger fragment sequences are known to those of skill in the art.

Two nucleic acid fragments are considered to "selectively hybridize" as described herein. The degree of sequence identity between two nucleic acid molecules affects the efficiency and strength of hybridization events between such molecules. A partially identical nucleic acid sequence will at least partially inhibit a completely identical sequence from hybridizing to a target molecule. Inhibition of hybridization of the completely identical sequence can be assessed using hybridization assays that are well known in the art (e.g., Southern blot, Northern blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a target nucleic acid sequence, and then by selection of appropriate conditions the probe and the target sequence "selectively hybridize," or bind, to each other to form a hybrid molecule. A nucleic acid molecule that is capable of hybridizing selectively to a target sequence under "moderately stringent" conditions typically hybridizes under conditions that allow detection of a target nucleic acid sequence of at least about 10–14 nucleotides in length having at least approximately 70% sequence identity with the sequence of the selected nucleic acid probe. Stringent hybridization conditions typically allow detection of target nucleic acid sequences of at least about 10–14 nucleotides in length having a sequence identity of greater than about 90–95% with the sequence of the selected nucleic acid probe. Hybridization conditions useful for probe/target hybridization where the probe and target have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

With respect to stringency conditions for hybridization, it is well known in the art that numerous equivalent conditions can be employed to establish a particular stringency by varying, for example, the following factors: the length and nature of probe and target sequences, base composition of the various sequences, concentrations of salts and other hybridization solution components, the presence or absence of blocking agents in the hybridization solutions (e.g., formamide, dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence. Also encompassed are polypeptide sequences which are immunologically identifiable with a polypeptide encoded by the sequence.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring gene sequences to target cells (e.g., viral vectors, non-viral vectors, particulate carriers, and liposomes). Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as viral vectors.

"Nucleic acid expression vector" refers to an assembly which is capable of directing the expression of a sequence or gene of interest. The nucleic acid expression vector includes a promoter which is operably linked to the sequences or gene(s) of interest. Other control elements may be present as well. For example, in addition to the components of an expression cassette, the plasmid construct may also include one or more bacterial origin(s) of replication, one or more selectable markers, a signal which allows the plasmid construct to exist as single-stranded DNA (e.g., a M13 origin of replication), a multiple cloning site, and a. "mammalian" origin of replication (e.g., a SV40 or adenovirus origin of replication).

An "expression cassette" comprises any nucleic acid construct which contains polynucleotide gene(s) or sequence(s) capable of being expressed in a cell. Expression cassettes may contain, in addition to polynucleotide gene(s) or sequence(s) of interest, additional transcriptional, translational or other regulatory or control elements. Such cassettes are typically constructed into a "vector," "vector construct," "expression vector," (i.e., a "nucleic acid expression vector") or "gene transfer vector," in order to transfer the expression cassette into target cells. Thus, the term includes cloning and expression vehicles, as well as viral vectors.

"Gram-positive" is a taxonomic feature referring to bacteria which resist decolorization with any standard Gram-staining dyes. In contrast, Gram-negative bacteria are easily decolotized with certain organic solvents such as ethanol or acetone. The ability of bacteria to retain or resist staining generally reflects the structure of the cell wall and it has been suggested that Gram-negative bacteria have more extensive peptidoglycan crosslinking and less permeable cells walls than their Gram-negative counterparts. Non-limiting examples of Gram-positive bacteria include: Stapholococcus, Streptococcus, certain Bacillus, Anthrax, Mycobacterium, etc.

"Light-generating" is defined as capable of generating light through a chemical reaction or through the absorption of radiation.

"Light" is defined herein, unless stated otherwise, as electromagnetic radiation having a wavelength of between about 300 nm and about 1100 nm.

"Visible light" is defined herein, unless stated otherwise, as electromagnetic radiation having a wavelength of between about 400 nm and about 750 nm.

"Light-generating protein" is defined as a protein or polypeptide capable of generating light through a chemical reaction (e.g., bioluminescence, as generated by luciferase) or through the absorption of radiation (e.g., fluorescence, as generated by Green Fluorescent Protein).

"Luciferase," unless stated otherwise, includes prokaryotic and eukaryotic luciferases, as well as variants possessing varied or altered optical properties, such as luciferases that produce different colors of light (e.g., Kajiyama, N., and Nakano, E., (1991) *Protein Engineering* 4(6):691–693. "Lux" refers to prokaryotic genes associated with luciferase and photon emission. "Luc" refers to eukaryotic genes associated with luciferase and photon emission.

"Animal" as used herein typically refers to a non-human mammal, including, without limitation, farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

"Analyte" as used herein refers to any compound or substance whose effects (e.g., induction or repression of a specific promoter) can be evaluated using the test animals and methods of the present invention. Such analytes include, but are not limited to, chemical compounds, pharmaceutical compounds, polypeptides, peptides, polynucleotides, and polynucleotide analogs. Many organizations (e.g., the National Institutes of Health, pharmaceutical and chemical corporations) have large libraries of chemical or biological compounds from natural or synthetic processes, or fermentation broths or extracts. Such compounds/analytes can be employed in the practice of the present invention.

MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

GENERAL OVERVIEW OF THE INVENTION

As discussed above, the synthesis of light in naturally occurring bioluminescent bacteria is encoded by five essential genes. These genes are clustered in an operon (luxCDABE) that can be moved into non-bioluminescent bacteria to produce a bioluminescent phenotype. Since all identified species of naturally occurring marine and terrestrial bioluminescent bacteria are Gram-negative however, the transformation of Gram-positive bacteria to bioluminescent phenotype has been limited, due in part to the differing genetics of these two bacterial groups. The present invention solves this problem in one aspect by reengineering the entire *Photorhabdus luminescens* lux operon to introduce Gram-positive control elements. This novel luxABCDE cassette was inserted into several different Gram-positive/negative shuttle vectors (pCMOR G+ series) and these constructs were then used as promoter-probe vehicles to select Gram-positive promoters which resulted in strong light production by the host bacterium. Using this approach several different genera of Gram-positive bacteria were made brightly bioluminescent, including several strains of *Staphylococcus aureus* and *Streptococcus pneumoniae*. In both the latter bacteria, as few as 100 colony-forming units (c.f.u.) could be detected at 37° C. using bioluminescence.

The luciferase enzyme is encoded by luxA and luxB, whereas the enzymes responsible for the aldehyde biosynthesis are encoded by the three genes luxC, luxD and luxE. However, since aldehyde can rapidly diffuse across cellular membranes and is commercially available e.g., Sigma), the genes encoding the synthesis of this substrate (luxCDE) are not an absolute necessity for bioluminescence and can be substituted by the addition of this compound exogenously. In order to generate a bioluminescent Gram-positive bacterium therefore, it is only necessary to ensure that the cell can synthesize a functional luciferase.

As discussed in the "Background of the Invention", this has been achieved in many Gram-positive bacteria by introducing a reengineered luxAB cassette in which a Gram-positive ribosome binding site (RBS) has been inserted upstream of luxA and this gene fused in-frame to luxB, so allowing the synthesis of a functional LuxAB fusion protein (Jacobs, M., et al., (1991) *Mol. Gen. Genet.* 230:251–256). Although this approach has been successful in generating a number of novel genera of bioluminescent Gram-positive bacteria that are useful for environmental studies (e.g., the assessment of food products for contamination by such bacteria), existing luxAB constructs are of limited use for studying pathogenicity, since none of the strains or constructs published to date produce enough light in vivo to make them useful for the in vivo monitoring applications discussed above.

The present invention relates to luciferase expression cassettes. These expression cassettes can then be inserted into a suitable backbone (e.g., a shuttle vector) and thereby confer the ability to produce light in a cell or animal. The expression cassettes described herein allow, for the first time, more than minimal amount of light to be produced from Gram-positive bacteria at physiological temperatures.

In one embodiment, the expression cassette contains bacterial lux genes recombinantly engineered to promote functional expression of lux, for example, by arranging the genes in the order luxABCDE. Thus, this cassette rearranges the unmodified order of these genes, namely luxCABDE. By including both the structural genes (luxAB) and substrate encoding genes (luxCDE), this expression cassette does not require the addition of exogenous substrate. Moreover, the rearrangement of genes together with the introduction of Gram+ Shine-Dalgarno sequences confers a greater light-producing ability than the unmodified order. A Gram-positive Shine-Dalgarno sequence is preferably inserted before (typically 5' to) more than one, or all of the rearranged lux genes. Optionally, short DNA sequences comprising promoters or other transcriptional or translational regulators are inserted before the lux cassette.

Another expression cassette provided by the present invention includes polynucleotides encoding luxAB, but not including the substrate encoding genes. When employing such luxAB expression cassettes, exogenous substrate, for example, aldehyde, is provided to monitor the ability to produce light. The luxAB expression cassettes typically include a DNA sequence which enhances translation between the genes encoding for luxA and luxB (for example, Shine-Dalgarno sequences).

In addition, another bacterial gene, luxY, isolated from *Vibrio fischeri* strain Y-1, encodes a yellow fluorescent protein (YFP), a substrate which emits yellow light with a lambda max of 545 nm when acted upon by the luciferase enzyme. See Baldwin, T. O., et al. (1990) *Biochem* 29:5509–5515. Accordingly, another expression cassette of the invention comprises polynucleotides encoding functional luxY. In one embodiment, the expression cassette includes polynucleotides encoding luxY and control elements, such as promoters and/or Shine-Dalgarno sequences, for example, from Gram-positive bacteria. The luxY expression cassettes may also contain DNA sequence encoding polypeptide sequences, where this polypeptide-encoding sequence is typically positioned between the promoter and the luxY-encoding sequence. In a further aspect of the invention, luxABCDEY, luxABY, etc., cassettes are provided. Adding the luxY gene to, for example, the luxABCDE gene cassette, results in broadening the range of wavelength of light emitted during bioluminescence towards the red end of the visible light spectrum. Given that longer-wavelength light more easily penetrates living tissue as compared to light of shorter wavelengths, selected embodiments of the luxABCDE gene cassette of the present invention (e.g., as described above) will therefore additionally include the luxY coding sequence, as a means of increasing the sensitivity of applications which employ bioluminescence as a reporter means.

Yet another expression cassette of the invention includes polynucleotides encoding functional luc, an eukaryotic luciferase gene. In one embodiment, the expression cassette comprises polynucleotides encoding luc and control elements, such as promoters and/or Shine-Dalgarno sequences, for example, from Gram-positive bacteria. The luc expression cassettes may also contain DNA sequence encoding polypeptide sequences, where this polypeptide-encoding sequence is typically positioned between the promoter and the luc-encoding sequence.

A variety of luciferase encoding genes have been identified including, but not limited to, the following: B. A. Sherf and K. V. Wood, U.S. Pat. No. 5,670,356, Kazami, J., et al., U.S. Pat. No. 5,604,123, S. Zenno, et al, U.S. Pat. No. 5,618,722; K. V. Wood, U.S. Pat. No. 5,650,289, K. V. Wood, U.S. Pat. No. 5,641,641, N. Kajiyama and E. Nakano, U.S. Pat. No. 5,229,285, M. J. Cormier and W. W. Lorenz, U.S. Pat. No. 5,292,658, M. J. Cormier and W. W. Lorenz, U.S. Pat. No. 5,418,155, de Wet, J. R., et al, (1987) *Molec. Cell. Biol.* 7:725–737; Tatsumi, H. N., et al, (1992) *Biochim. Biophys. Acta* 1131:161–165 and Wood, K. V., et al, (1989) *Science* 244:700–702, all herein incorporated by reference. Such luciferase encoding genes may be modified by the methods described herein to produce polypeptide sequences and/or expression cassettes useful, for example, in Gram-positive microorganisms.

Also provided are methods of screening for sequences which enhance luciferase expression using the expression cassettes described herein. As noted, various sequences can be inserted into these expression cassettes (e.g., between the luxA and luxB encoding nucleotides or between luc and the promoter sequence). Either before or after insertion of such sequences, the expression cassettes can be introduced into a suitable vector backbone, for example a shuttle vector. Subsequently, light-producing ability conferred by the expression cassette and inserted sequence to a particular cell type (for example a related microbe or mammalian cell) can be evaluated.

In another aspect, the expression cassettes are useful in methods of monitoring cells (e.g., prokaryotic and eukaryotic) in culture systems. In one embodiment, a luciferase expression cassette described herein is introduced into Gram-positive bacteria and the effect of analytes on these cells monitored by their ability to produce light. In this way, for example, antibiotics can be readily screened in cells for their ability to kill or suppress growth of the cells. As described above, certain expression cassettes (e.g., luxAB and luc) require the addition of exogenous substrate. Thus, the invention also includes methods of administering a substrate (e.g., aldehyde), for example by adding aldehyde vapor to the atmosphere in contact with a culture medium containing the cells carrying the expression cassettes of the present invention.

Alternatively, the expression cassettes (i.e., including a suitable backbone) of the invention can be introduced into a whole animal. In one embodiment, expression cassettes are first introduced into cells, for example, Gram-positive bacteria. The effect of an analyte on Gram-positive bacteria in whole animals can then be evaluated. When exogenous substrate (e.g., aldehyde) is required, it may be provided to the animal, for example, by injection or by allowing the animal to breath in aldehyde vapor and these methods are also provided.

Further, the expression cassettes of the present invention can be used to create transgenic animals.

Advantages of the present invention include, but are not limited to, (i) obtaining high levels of luciferase (lux or luc) expression in virulent strains of bacteria, particularly Gram-positive bacteria, which, for example, allows monitoring of infections in cells; (ii) obtaining high levels of luciferase (lux or luc) expression in virulent strains of bacteria, particularly Gram-positive bacteria, which, for example, allows monitoring of infections when using luciferase as a reporter gene in a cell or animal system; (iii) expression of the substrate-coding genes of lux eliminates the need for addition of exogenous substrate; (iv) rearrangement of lux operon from CDABE to ABCDE allows for separation of functional components of the operon (e.g., separately transform with lux AB and/or lux CDE components).

Luciferases

Bioluminescence provides a powerful reporter system for studying bacterial infection (e.g., U.S. Pat. No. 5,650,135). Luciferase is a term applied to members of a family of diverse enzymes which share the property of producing light when provided with a substrate (e.g., luciferin, longchain aldehyde or colentrazine), an energy source (e.g., ATP or FMNH$_2$) and oxygen. Luciferases can be broadly classified into eukaryotic luciferases and prokaryotic luciferases. Eukaryotic luciferase ("luc") is typically encoded by a single gene (see, e.g., de Wet, J. R., et al., (1985), *Proc. Natl. Acad. Sci. U.S.A.* 82:7870–7873; de Wet, J. R, et al., (1987) *Mol. Cell. Biol.* 7:725–737). An exemplary eukaryotic organism containing a luciferase system is the North American firefly *Photinus pyralis*. Firefly luciferase has been extensively studied, and is widely used in ATP assays. cDNAs encoding luciferases from *Pyrophorus plagiophthalamus*, another species of click beetle, have been cloned and expressed (Wood, et al.). This beetle is unusual in that different members of the species emit bioluminescence of different colors. Four classes of clones, having 95–99% homology with each other, were isolated. They emit light at 546 nm (green), 560 nm (yellow-green), 578 nm (yellow) and 593 nm (orange). The last class (593 nm) may be particularly advantageous for use as a light-generating moiety with the present invention, because the emitted light has a wavelength that penetrates tissues more easily than shorter wavelength light.

Bacterial luciferase ("lux") is typically made up of two subunits (α and β) encoded by two different genes (luxA and luxB) on the lux operon. Three other genes on the operon (lux C, lux D and luxE) encode the enzymes required for biosynthesis of the aldehyde substrate. Bacterial lux is present in certain bioluminescent Gram-negative bacteria (e.g., *Photorhabdus luminescens*) and is ordered CDABE.

Luciferase Expression Cassettes

A variety of luciferase encoding genes have been identified including, but not limited to, the following: B. A. Sherf and K. V. Wood, U.S. Pat. No. 5,670,356, Kazami, J., et al., U.S. Pat. No. 5,604,123, S. Zenno, et al, U.S. Pat. No. 5,618,722; K. V. Wood, U.S. Pat. No. 5,650,289, K. V. Wood, U.S. Pat. No. 5,641,641, N. Kajiyama and E. Nakano, U.S. Pat. No. 5,229,285, M. J. Cormier and W. W. Lorenz, U.S. Pat. No. 5,292,658, M. J. Cormier and W. W. Lorenz, U.S. Pat. No. 5,418,155, de Wet, J. R., et al, (1987) *Molec. Cell. Biol.* 7:725–737; Tatsumi, H. N., et al, (1992) *Biochim. Biophys. Acta* 1131:161–165 and Wood, K. V., et al, (1989) *Science* 244:700–702, all herein incorporated by reference.

Lux-encoding Expression Cassettes

In one aspect of the invention, expression cassettes comprising polynucleotides encoding both the structural and substrate-encoding lux gene-products are provided. The present inventors have determined that rearranging the lux genes, for example, from CABDE to ABCDE and inserting Gram-positive Shine-Dalgarno sequences before one or more of the lux genes confers on the resulting luciferase an enhanced ability to produce light. Suitable Gram-positive Shine-Dalgarno sequences (e.g., SEQ ID NO:1) will be known to those of skill in the art in view of the teachings of the specification, and are also described in the Examples below. The luxABCDE expression cassettes express not only luciferase, but also the biosynthetic enzymes necessary for the synthesis of the lux luciferase's substrate—aldehyde. Accordingly, oxygen is the only extrinsic requirement for bioluminescence when this expression cassette is used.

In another aspect, luxAB expression cassettes are provided. The luxAB cassettes typically contain a Gram-positive ribosome binding site (also referred to as a "Shine-Dalgarno sequence) operably linked upstream of each of the polynucleotides encoding luxA and B. As described herein, these cassettes confer higher levels of luciferase activity than found in known constructs, particularly when expressed in Gram-positive bacteria such as Stapholococcus or Streptococcus.

Both the luxABCDE and luxAB expression cassettes described herein optionally contain a site for insertion of known or unknown sequence. In both cassettes, the insertion site is typically located 5' to the luxB gene (i.e., between luxA and luxB). Using this insertion site, a random fragment expression enhancing sequence screen (RFEESS), for instance as described in the Examples, can be conducted by doing (1) partial enzymatic digestions (e.g., using SauIIIa) of a DNA of interest, e.g., DNA obtained from Gram-positive bacteria; (2) inserting these fragments 5' to the luxB gene; (3) cloning these polynucleotide fragments into suitable vectors containing the lux expression cassettes; (4) transforming them into cells (e.g., Gram-positive bacteria) and (5) evaluating them for their ability to luminesce.

Luc-encoding Expression Cassettes

The present invention also includes expression cassettes that allow for expression of eukaryotic luciferase. In one embodiment, the luc expression cassette includes a polynucleotide encoding the luc gene product operably linked to a constitutively expressed promoter. Preferably, the promoter is obtained from a Gram-positive bacteria. The expression cassette can then be introduced into a suitable vector backbone, for example as a shuttle vector. In one embodiment, the shuttle vector includes a selectable marker and two origins of replication, one for replication in Gram-negative organisms, and the other for replication in Gram-positive organisms.

Appropriate promoters can be identified by any method known in the art in view of the teachings of the present specification. In one such method, described above and below in the Examples, a random fragment expression enhancing sequence screen (RFEESS) is conducted using partially digested DNA (e.g., using SauIIIa) obtained from Gram-positive bacteria. The random fragments are then cloned into vectors containing luc, transformed into bacteria, preferably Gram-positive bacteria, and evaluated for their ability to cause luminescence.

Methods of Making Luciferase Expression Vectors

In a preferred embodiment of the present invention, the luciferase expression cassettes are inserted into a vector backbone, e.g., a shuttle vector, such as pMK4 (Sullivan, M., et al., (1984) *Gene* 29:21–26), pDL289 (Buckley, N., et al., (1995) *J. Bacteriol* 177:5028–5034) and the pSUM series (Ainsa, J. A., et al., (1996) *Gene* 176:23–26). Typically, the shuttle vectors include the following: (1) a Gram-positive origin of replication; (2) a Gram-negative origin of replication (3) polylinkers; and (4) a polynucleotide encoding a selectable marker (e.g., ampicillin, chloramphenicol).

The expression cassettes described herein can be constructed utilizing methodologies known in the art of molecular biology (see, for example, Ausubel, F. M., et al., *Current Protocols in Molecular Biology*, John Wiley and Sons, Inc., Media, Pa. (1995), or Sambrook, et al.) in view of the teachings of the specification. Typically, expression cassettes are assembled from polynucleotides encoding lux or luc genes by operably linking these polynucleotides to suitable transcriptional (e.g., a promoter) and translational regulatory elements (e.g., Gram-positive Shine-Dalgarno sequences). Short, random nucleotide sequences, selectable markers, and the like can also be introduced into the expression cassettes at suitable positions.

A preferred method of obtaining polynucleotides, suitable regulatory sequences and short, random nucleotide sequences is PCR. General procedures for PCR as taught in MacPherson et al., PCR: *A Practical Approach*, (IRL Press at Oxford University Press, (1991)). PCR conditions for each application reaction may be empirically determined. A number of parameters influence the success of a reaction. Among these parameters are annealing temperature and time, extension time, Mg2+ and ATP concentration, pH, and the relative concentration of primers, templates and deoxyribonucleotides. Exemplary primers are described below in Example 1. After amplification, the resulting fragments can be detected by agarose gel electrophoresis followed by visualization with ethidium bromide staining and ultraviolet illumination.

Another method for obtaining polynucleotides, for example, short, random nucleotide sequences, is by enzymatic digestion. As described below in the Examples, short DNA sequences generated by digestion of DNA from a suitable bacterium with, e.g., a blunt-cutting four-nucleotide recognition restriction enzyme such as AluI, HaeIII and Sau3AI, were ligated with the modified lux cassette.

Polynucleotides are inserted into vector genomes using methods known in the art. For example, insert and vector DNA can be contacted, under suitable conditions, with a restriction enzyme to create complementary or blunt ends on each molecule that can pair with each other and be joined with a ligase. Alternatively, synthetic nucleic acid linkers can be ligated to the termini of a polynucleotide. These synthetic linkers can contain nucleic acid sequences that correspond to a particular restriction site in the vector DNA. Other means are known and available in the art as well.

Evaluation of Luciferase Expression Cassettes in Cell Culture

Luciferase vector constructs such as the ones described above and in the Examples, can be adapted for use in transforming a variety of host cells, including most bacteria (e.g., Gram-positive bacteria, Gram-negative bacteria), and many eukaryotic cells (including, but not limited to microorganisms, plant cells, mammalian cells). In addition, certain viruses, such as herpes virus and vaccinia virus, can be genetically-engineered to express luciferase. For example, Kovacs, et al. teach the stable expression of the gene encoding firefly luciferase in a herpes virus. Brasier, et al., teach the use of luciferase gene constructs in mammalian cells. Luciferase expression from mammalian cells in culture has been studied using CCD imaging both macroscopically (Israel, H., (1991) *Gene* 104:139–145) and microscopically (Hooper, C., et al., (1990) *Journal of Bioluminescence and Chemiluminescence* 5:123–130).

Thus, cells, both prokaryotic and eukaryotic, are useful targets for the expression cassettes of the present invention. Cells can be loaded with relatively high concentrations of expression cassettes, provided by, for example, a heterologous genetic construct used to transform the cells. In addition, cells can be selected that express "targeting moieties", or molecules effective to target them to desired locations within the subject. Alternatively, the cells can be transformed with a vector construct expressing an appropriate targeting moiety.

Transformation methods for both prokaryotic cells and eukaryotic cells are well known in the art (e.g., Sambrook, et al.) and include, but are not limited to, calcium phosphate precipitation, microinjection or electroporation. Vectors containing the appropriate regulatory elements and multiple cloning sites are widely commercially available (e.g., Stratagene, La Jolla, Calif.; Clontech, Palo Alto, Calif.).

Use of Luciferase Vectors as Reporters in Cell Cultures

The expression cassettes described herein are useful reporter systems in both prokaryotic and eukaryotic cells. By monitoring luminescence, promoters and analytes can be evaluated in cell culture systems. For example, a promoter obtained from a gene whose induction is associated with drug resistance can be operatively linked to a luciferase expression cassette described herein (e.g., luxAB or luxABCDE). The expression cassettes are introduced into cells (e.g., by shuttle vector) and effectiveness of analytes evaluated by monitoring luminescence.

Tumorigenicity can also be evaluated using the luciferase expression cassettes described herein. For example, eukaryotic cells (e.g., *Candida albicans*, Giardia and tumor cells) can be transformed with luciferase expression cassettes containing a regulatable promoter that is expressed under certain conditions, for example upon infection of the cell with a virus or stimulation by a cytokine. Promoters that respond to factors associated with these and other stimuli are known in the art. In a related aspect, inducible promoters, such as the Tet system (Gossen, et al.) can be used to transiently activate expression of the light-generating protein. For example, the luxABCDE expression cassette can be operatively linked to tumor associated promoters and the cells transformed with this cassette used to screen for anti-tumor compounds.

Evaluation of Luciferase Expression Vectors in Animals

The expression cassettes described herein are particularly useful for non-invasive imaging of whole animals. Non-invasive imaging of whole animals is described in co-owned U.S. Pat. No. 5,650,135, by Contag, et al., and herein incorporated by reference. (see, also, Contag, et al., (1998) *Nature Medicine* 4(2):245–247; Contag, et al., (1996) *OSA Tops on Biomedical Optical Spectroscopy and Diagnostics* 3:220–224; Contag, et al., (1997) *Photochemistry and Photobiology*, 66(4):523–531; and Contag, et al., (1995) *Mol. Microbiol.* 18:593–603.

In the imaging method, the conjugates contain a biocompatible entity (e.g., a transformed bacterium) and a light-generating moiety (e.g., a luciferase enzyme). Light-emitting conjugates are typically administered to a subject by any of a variety of methods, allowed to localize within the subject, and imaged. Since the imaging, or measuring photon emission from the subject, may last up to tens of minutes, the subject is typically, but not necessarily, immobilized during the imaging process.

Imaging of the light-emitting entities involves the use of a photo detector capable of detecting extremely low levels of light—typically single photon events—and integrating photon emission until an image can be constructed. Examples of such sensitive photo detectors include devices that intensify the single photon events before the events are detected by a camera, and cameras (cooled, for example, with liquid nitrogen) that are capable of detecting single photons over the background noise inherent in a detection system.

Once a photon emission image is generated, it is typically expressed as a pseudocolor image superimposed on a "photographic" reflected light image of the subject to provide a frame of reference for the source of the emitted photons (i.e. localize the light-emitting conjugates with respect to the subject). Such a "composite" image is then analyzed to determine the location and/or level of expression of a reporter gene in the subject.

Infection of Animals

The luciferase expression cassettes described herein are useful in evaluating both prokaryotic and eukaryotic cells in an animal. Pathogenic bacteria (e.g. Gram-positive bacteria) can be conjugated and/or transformed with the luciferase expression cassettes described herein and subsequently introduced into a whole animal. The animal can then be used to follow the infection process in vivo and to evaluate potential anti-infective drugs, such as new antibiotics, for their efficacy in inhibiting the infection. Thus, in one aspect, the expression cassettes described herein are useful in non-invasive imaging and/or detecting of light-emitting conjugates in mammalian subjects infected with bacteria carrying a luciferase expression cassette. By way of example, the luciferase expression cassettes can be used to screen agents useful in inhibiting the growth and/or proliferation of pathogenic bacteria.

In addition, it is possible to obtain *E. coli* libraries containing bacteria expressing surface-bound antibodies which can be screened to identify a colony expressing an antibody against a selected antigen (Stratagene, La Jolla, Calif.). Bacteria from this colony can then be transformed with a luciferase expression cassette of the present invention, and transformants can be utilized in the methods of the present invention, as described above, to localize the antigen in a mammalian host.

Alternatively, the transformed cells may be administered to a test subject such that they become uniformly distributed in the subject. Further, a regulatable promoter may be employed in the expression cassette such that the light-generating protein is expressed under certain conditions, for example upon infection by a virus or stimulation by a cytokine. Promoters that respond to factors associated with these and other stimuli are known in the art. In a related aspect, inducible promoters, such as the Tet system (Gossen, et al.) can be used to transiently activate expression of the light-generating protein.

For example, CD4+ lymphatic cells can be transformed with a construct containing tat-responsive HIV LTR elements, and used as an assay for infection by HIV (Israel, H., (1991) *Gene* 104:139–145). Cells transformed with such a construct can be introduced into SCID-hu mice (McCune, et al, (1997) *Science* 278:2141–2) and used as model for human HIV infection and AIDS.

Tumor cell lines transformed as above, for example, with a constitutively-active promoter, may be used to monitor the growth and metastasis of tumors. Transformed tumor cells may be injected into an animal model, allowed to form a tumor mass, and the size and metastasis of the tumor mass monitored during treatment with putative growth or metastasis inhibitors.

Tumor cells may also be generated from cells transformed with constructs containing regulatable promoters, whose activity is sensitive to various infective agents, or to therapeutic compounds.

Transgenic Animals

The expression cassettes described herein can be used to generate transgenic animals. Methods of generating transgenic, non-human animals are known in the art (Leder, P., et al, U.S. Pat. No. 4,736,866; Melmed, S., et al., U.S. Pat. No. 5,824,838; Bosch; F., et al, U.S. Pat. No. 5,837,875; Capecchi, M. R., et al, U.S. Pat. No. 5,487,992; Bradley, A., et al, U.S. Pat. No. 5,614,396; Ruley, H. E., U.S. Pat. No. 5,627,058, all herein incorporated by reference).

Substrate Administration

As described above, certain expression cassettes described herein require the addition of exogenous substrate for the production of light (e.g., luc and luxAB expression cassettes). In a preferred embodiment of the present invention, the substrate is aldehyde. When administered to cells, aldehyde may be applied in the atmosphere surrounding the culture media as a vapor or directly to the culture media as a liquid or solid.

In addition, the substrate may also be administered to the whole animals. Appropriate concentrations for the substrate can be empirically determined for each line of test animal constructed. The substrate (typically, luciferin or aldehyde) can be administered before, concomitantly with, or after the administration of the analyte of interest. The routes of administration of the substrate can be as described for the analyte. Preferred routes of administration for the substrate include, but are not limited to, intravenous or topical administration or by providing substrate in the atmosphere, for example, as a vapor.

The following examples are intended to illustrate, but not limit this invention.

Materials and Methods

Unless indicated otherwise, manipulation of cells, proteins and nucleic acids (e.g., DNA) were performed using standard methods, as described in, e.g., Sambrook, et al., and Ausubel, F. M., et al., *Current Protocols in Molecular Biology*, John Wiley and Sons, Inc., Media, Pa. (1995). Unless indicated otherwise, restriction enzymes were obtained from New England Biolabs, modifying enzymes were obtained from Promega or Boehringer Mannheim, and other laboratory chemicals were obtained from Sigma Chemical Company (St. Louis, Mo.).

In Vitro Screening in Presence of Exogenous Aldehyde

Screening using aldehyde. Exogenous aldehyde substrate was added prior to imaging plates or cultures of bacteria not containing the luxCDE genes. For imaging plates, n-decyl aldehyde (decanal; Sigma Chemical Company) was spread on the inside, surface of lids covering the plates containing the bacteria to be imaged ("aldehyde vapor imaging"), and the plates then imaged using an intensified CCD camera (Hamamatsu Photonics model 2400-32) essentially as described in U.S. Pat. No. 5,650,135. For imaging liquid cultures, 1 $\mu$l of decanal was added to 1 ml. of the appropriate 10-fold dilutions of the culture.

B. Preparation of DNA and Cloning

Unless indicated otherwise, following digestion with one or more restriction endonucleases, DNA samples were heated to 85° C. for 15 min to inactivate the restriction enzymes. Ligations were performed at 16° C. overnight.

C. Transformation of Bacterial Cells

Preparation of Competent Cells. Unless indicated otherwise, bacterial cells were transformed as follows. Bacterial cultures were grown overnight in LB. Five mls. of each culture were used to inoculate fresh 500 mls. volumes of LB. These cultures were shaken at 37° C. until an O.D (600 nm) of approximately 0.6 was reached. The cells were then chilled on ice for 30 min before being harvested by centrifugation at 3,000×g for 10 min at 4° C. The cells were resuspended in 50 mls. of either cold 0.5 M sucrose (*S. aureus*) or ddH$_2$O (*E. coli*), before being re-centrifuged and resuspended in 5 mls. of either cold 0.5 M sucrose (*S. aureus*). or ddH$_2$O (*E. coli*). At this stage, the cells were held on ice for 30 min, and then re-centrifuged and resuspended in 5 mls. of cold 10% glycerol. Aliquots of each cell type were frozen down and stored at −80° C.

Electroporation. Plasmid DNA was purified using a Qiagen column, dialyzed, and electroporated into competent cells using a "GenePulser" (BioRad). The settings were 25 µF, 2.5 kV, and either 100 ohms resistance for *S. aureus*, or 400 ohms resistance for *E. coli* and *S. pneumoniae*. The cells were left to recover in 1 ml. of culture medium 2 hr at 37° C. before being plated on a suitable agar containing the requisite selection antibiotic.

D. Imaging Samples

Samples were imaged essentially as described in Contag, et al., U.S. Pat. No. 5,650,135, with minor modifications as indicated below. In experiments performed in support of the present invention (detailed below), the amount of light generated by a sample was quantified using either an intensified photon-counting camera (Hamamatsu Photonics Model 2400-32) or a cooled integrating camera (Princeton Instruments Model LN/CCD 1340-1300-EB/1). Unless indicated otherwise, the photon-counting camera was camera XEN-3 and the integrating camera was camera XEN-5, both located at Xenogen Corporation, Alameda, Calif. Both types of cameras use a charge-coupled device array (CCD array), to generate a signal proportional to the number of photons per selected unit area. The selected unit area may be as small as that detected by a single CCD pixel, or, if binning is used, that detected by any selected group of pixels. This signal may optionally be routed through an image processor, such as the Argus available from Hamamatsu Photonics, and is then transmitted to a computer (either a PC running Windows NT (Dell Computer Corporation; Microsoft Corporation, Redmond, Wash.) or a Macintosh (Apple Computer, Cupertino, Calif.) running an image-processing software application, such as "LivingImage" (Xenogen Corporation, Alameda, Calif.)). The software and/or image processor are used to acquire an image, stored as a computer data file. The data generally take the form of (x, y, z) values, where x and y represent the spatial coordinates of the point or area from which the signal was collected, and z represents the amount of signal at that point or area, expressed as "Relative Light Units" (RLUs).

To facilitate interpretation, the data are typically displayed as a "pseudocolor" image, where a color spectrum is used to denote the z value (amount of signal) at a particular point. Further, the pseudocolor signal image is typically superimposed over a reflected light or "photographic" image to provide a frame of reference.

It will be appreciated that if the signal is acquired on a camera that has been calibrated using a stable photo-emission standard (available from, e.g., Xenogen Corporation), the RLU signal values from any camera can be compared to the RLUs from any other camera that has been calibrated using the same photo-emission standard. Further, after calibrating the photo-emission standard for an absolute photon flux (photons emitted from a unit area in a unit of time), one of skill in the art can convert the RLU values from any such camera to photon flux values, which then allows for the estimation of the number of photons emitted by a transformed cell in the sample per unit time.

E. Quantification of Light Output Using 96-Well Microtiter Plates

The amount of light generated by cells in solution was quantified by plating dilutions of the solution into wells of a 96-well plate, and imaging the plate as described above in the Xen-3 camera. The LivingImage software was then used to superimpose defined borders around the each area of the image showing a signal corresponding to light from a particular well. The signal from each of these areas was then quantified, and expressed as a single RLU value for each well. These RLUs were used in several of the studies detailed below, including Examples 13, 14 and 15.

EXAMPLE 1

Incorporation of Gram-positive RBS Upstream of LuxA, B, C, D and E.

The five genes of the *Photorhabdus luminescens* lux operon, lux A–E, were PCR amplified using the polymerase chain reaction (PCR; Mullins; Mullins, et al.) to incorporate the sequence of the Gram-positive ribosome binding site (RBS) AGGAGG (SEQ ID NO:1) such that this site was at least seven nucleotides upstream of each start codon. Each of the lux genes was amplified individually using the primer sets shown in Table 1, below. In each case, nucleotides highlighted in bold show the position and sequence of the different restriction endonucleotides (identified in far-right column) incorporated to facilitate cloning. Gram-positive RBSs and start codons are underscored by solid and broken lines, respectively.

TABLE 1

| Gene | Primer | SEQ# | Sequence | Restriction Sites |
|------|--------|------|----------|-------------------|
| luxA | XAF3 | 2 | CCCCGGATCCTGCAGATGAAGCAAGAGGAGGACTCTCTATG | BamH I, Pstl I |
|      | XAR  | 3 | GGCGGATCCGTCGACTTAATATAATAGCGAACGTTG | BamH I, Sal I |
| luxB | XBF  | 4 | GGGAATTCTCGAGGAGGAGAGAAAGAAATGAAATTTGGA | EcoR I, Xho I |
|      | XBR  | 5 | GGCGGATCCGTCGACTTAGGTATATTCCATGTGGTAC | BamH I, Sal I |
| luxC | XCF  | 6 | GGGAATTCTCGAGGAGGATGGCAAATATGACTAA | EcoR I, Xho I |
|      | XCR  | 7 | GGCGGATCCGTCGACTTATGGGACAAATACAAGGAAC | BamH I, Sal I |
| luxD | XDF  | 8 | GGGAATTCTCGAGGAGGAGTAAAAGTATGGAAAATGA | EcoR I, Xho I |
|      | XDR  | 9 | GGCGGATCCGTCGACTTAAGACAGAGAAATTGCTTGA | BamH I, Sal I |
| luxE | XEF  | 10 | GGGAATTCTCGAGGAGGAAAACAGGTATGACTTCATATG | EcoR I, Xho I |
|      | XER  | 11 | GGCGGATCCGTCGACTTAACTATCAAACGCTTCGGTTA | BamH I, Sal I |

PCR was performed with an automated thermocycler (Techne Progene, Princeton, N.J.) with 200 µl thin walled PCR tubes (Molecular BioProducts, San Diego, Calif.). Reactions were carried out in 50 µl volumes containing 5 µl of 10×PCR buffer (supplied with Taq DNA polymerase obtained from Roche Molecular Biochemicals (Switzerland)), 2.0 mM $MgCl_2$, 50 pmol of each oligonucleotide primer (Operon; see Table 1 for sequences), 0.2 mM of each deoxynucleotide triphosphate (dATP, dCTP, dGTP, dTTP; Amersham Pharmacia Biotech, (Uppsala, Sweden)), 1 U of Taq DNA polymerase Roche Molecular Biochemicals (Switzerland), and 10 ng of plasmid DNA containing the *P. luminescens* luxCDABE cassette (either pSB417 or pSB384; Winson, et al., (1998), *FEMS*, 163:185–202). Amplification of each gene was achieved using 30 cycles at 95° C. for 15 sec., 50° C. for 30 sec., and 72° C. for 1 min., followed by a final extension step at 72° C. for 2 min.

The sequence of the *Photorhabdus luminescens* (formerly referred to as *Xenorhabdus luminescens*) luxCDABE cassette is available from GenBank, under accession number M90092.1 (GI: 155411; XENLABCDEB) (Meighen, E. A. and Szittner, R. *J. Bacteriol.* 174:5371–5381 (1992)).

EXAMPLE 2

Construction of pSK⁻G+LuxAG+LuxB (LuxAB Cassette in pBluescript)

The genes amplified in Example 1, above, were individually assembled on pBluescript SK⁻ vectors (Stratagene, LaJolla, Calif.). The luxA PCR product was digested with BamH I/Sal I and ligated into pBluescript SK⁻ at the BamH I/Sal I sites (directionally orientated downstream of the IPTG-inducible lacZ promoter), generating plasmid pSK⁻G+luxA. Plasmid pSK⁻G+luxA was then electroporated into DH5α *E. coli* (Stratagene), and the cells were plated on LB agar plates containing 100 μg/ml ampicillin. Selected colonies were grown up for plasmid preps, and the plasmid DNA was isolated and cut with Sal I. The resulting fragments were ligated with Sal I/Xho I-cut luxB PCR amplified DNA (Example 1) to generate pSK⁻G+luxAG+luxB.

pSK⁻G+luxAG+luxB was electroporated into DH5α *E. coli* cells, plated on LB agar containing 100 μg/ml ampicillin and the resulting transformants screened for light in the presence of exogenous aldehyde (see Materials and Methods) using a photon-counting CCD camera (Hamamatsu Photonics, Shizuoka Pref., Japan; model 2400-32). Bioluminescent colonies were purified and monitored for their light intensity. Extremely high levels of bioluminescence were recorded (camera sensitivity only reaching 2.0). Even in the absence of exogenous aldehyde, background levels of light could be detected in both solution and from plates (switching the bit range from 0–5 in 1 min in the latter case). Surprisingly, the level of light from the Gram-negative *E. coli* colonies containing pSK⁻G+luxAG+luxB was significantly greater (in the presence of exogenous aldehyde) than the level of light from *E. coli* colonies transformed with the native *Photorhabdus luminescens* lux operon.

These results show that functional *Photorhabdus luminescens* luciferase α and β subunits can be individually expressed in Gram-negative bacteria (e.g., *E. coli*) from a DNA expression cassette driven by the lacZ promoter, where the DNA expression cassette contains Gram-positive Shine-Dalgarno sequences upstream of each of the luxA and lux B coding sequences.

EXAMPLE 3

Construction of pSK⁻LuxABCDE (LuxABCDE Cassette in pBluescript)

Assembly of a separate luxCDE cassette in pBluescript SK⁻ was achieved by the sequential cloning of luxC, luxD and luxE essentially as described in Example 2 for the generation of the luxAB cassette. The luxC–E PCR amplification products were individually digested with the compatible enzymes SalI and XhoI, and each step of the cloning procedure was confirmed by PCR of the *E. coli* transformants. The fidelity of the final luxCDE cassette was confirmed by inserting this sequence, cut with Sal I/Xho I, at the Sal I site downstream of the luxAB genes in pSK⁻G+luxAG+luxB, generating pSK⁻luxABCDE. Screening was performed as described above, except that no aldehyde treatment was performed, since the substrate was encoded by the luxCDE genes. As above, *E. coli* DH5α containing pSK⁻luxABCDE were considerably brighter than bacteria containing the native *Photorhabdus luminescens* lux operon.

EXAMPLE 4

Construction of pMK4LuxAB and pMK4LuxABCDE Shuttle Vectors, and Evaluation of their Bioluminescence Properties in *Staphylococcus aureus*

A. Construction of pMK4LuxAB Shuttle Vector

The luxAB cassette generated as described in Example 2, above, was isolated from pSK⁻G+luxAG+luxB via a BamH I/Sal I digest and cloned into the BamH I/Sal I sites of the Gram-positive/negative shuttle vector pMK4 (Sullivan, M., et al., (1984), "New shuttle vectors for *Bacillus subtilis* and *Escherichia coli* which allow rapid detection of inserted fragments", *Gene* 29:21–26, incorporated herein by reference). pMK4 is available from the American Type Culture Collection (ATCC; Manassas, Va.) under ATCC Number 37315. The cloning was carried out such that (i) the luxAB cassette was oriented to oppose the IPTG inducible lacZ promoter, and (ii) a BamH I restriction site was maintained upstream of the luxA coding region. The resulting vector (pMK4luxAB) construct was electroporated into DH5α and plated on LB containing 100 μg/ml ampicillin.

B. Random Fragment Expression Enhancing Sequence Screen (RFEESS) Using pMK4LuxAB Plasmid and Exogenous Aldehyde Vapor To screen for suitable Expression Enhancing Sequences (EESs) (e.g., promoter sequences), *Staphylococcus aureus* genomic DNA was cut with Sau3 A in a partial digest (see, e.g., Ausubel, F. M., et al., *Current Protocols in Molecular Biology*, John Wiley and Sons, Inc., Media, Pa. (1995)) and ligated into the pMK4luxAB plasmid that had been cut with BamH I. Five different DNA concentrations were digested (1 μg/μl, 500 ng/μl, 200 ng/μl, 100 ng/μl and 50 ng/μl) in sets of 4×0.6 log enzyme dilutions (starting with 4U Sau3A into a 20 μl DNA dilution). The 20 separate ligations were then electroporated into *S. aureus* RN4220, pooled, incubated for 2 h and plated on BHI containing 5 μg/ml chloramphenicol. Approximately 20,000 colonies (100 plates with 200 colonies) were screened for light in the presence of exogenous aldehyde. This resulted in the isolation of 73 highly bioluminescent transformants (pMK4luxABSa1–Sa73; abbreviated as Sa1–Sa73 in Table 2, below).

These isolates were colony purified and graded according to their bioluminescence on LB plates in the presence of aldehyde vapor. Each plate was placed under the CCD camera and graded during continuous monitoring (i.e., without collecting data). Grading was in the order Off Scale—OS (camera sensitivity automatically switching down to the number indicated), Very High—VH (on the upper limits of normal camera detection at sensitivity 10), High—H (some areas continuously flashing red), Medium—M (high frequency of hits), Low—L (low frequency of hits).

TABLE 2

| Brightness | EXPRESSION-ENHANCING SEQUENCE IDENTIFIERS |
|---|---|
| OS3 | Sa3 |
| OS4 | Sa6 |
| OS5 | Sa5, Sa7, Sa21 |
| OS6 | Sa4, Sa8, Sa13, Sa14, Sa19, Sa20 |
| OS7 | Sa1, Sa12, Sa17 |
| OS8 | Sa9, Sa10, Sa11, Sa22 |
| OS9 | Sa15, Sa16, Sa18, Sa23, Sa24 |
| VH | Sa2, Sa25–Sa29 |
| H | Sa30–Sa46 |
| M | Sa47–Sa58 |
| L | Sa59–Sa73 |

C. Addition of LuxCDE Genes to pMK4LuxAB to Generate pCMOR G+1 (pMRK4) Shuttle Vectors The luxCDE genes were introduced into pMK4luxABSa1–Sa6 to generate plasmid family pMK4luxABCDESa1–Sa6 (renamed pCMOR G+1 Sa1–Sa6 or pMK4 luxABCDE P1–P6) as follows: Plasmids Sa1–Sa6 were reamplified in *E. coli* DH5α and cut with Sal I. These digests were then individually ligated with Xho I/Sal I cut luxCDE (with the Xho I site at the 5' end and the Sal I site at the 3' end of the luxCDE cassette), which was PCR-amplified (35 cycles of 95° C. 30", 50° C. 1' and 72° C. 3') from pSK luxCDE using M13 (–20) and M13 reverse primers (see, e.g., 1999 Stratagene Catalog, page 320 for sequences). A map representative of the resulting plasmids (minus EESs Sa1–Sa6, with the BamH I insertion site substituted for the Sa1–6 sequences shown instead) is illustrated in FIG. 1.

The six ligations were electroporated into *S. aureus* RN4220 and plated on LB plates containing 5 μg/ml chloramphenicol, and resulting colonies were screened for light in the absence of exogenous aldehyde. Interestingly, the levels of bioluminescence recorded from the Sa1–Sa6 luxABCDE transformants differed from the corresponding luxAB transformants. The EES which resulted in the lowest levels of bioluminescence in the pMK4 luxAB construct (Sa2) produced the brightest signal when used in the lux-ABCDE construct.

The plasmids giving the most light in *S. aureus* RN4220, pMK4 luxABCDE Sa2 (pCMOR G+1 Sa2) and pMK4 luxABCDE Sa4 (pCMOR G+1 Sa4), were mini-prepped and electroporated into the pathogenic isolate 8325-4 of *S. aureus*. The resulting transformants were highly bioluminescent (light levels comparable to those achieved with engineered Gram-negative bacteria). Plasmid pMK4 luxAB-CDE Sa2 (pCMOR G+1 Sa2; a.k.a pXGN-lux-1) in *S. aureus* strain 8325-4 (transformed strained termed StaphA-XGN-1) was deposited on Jun. 15, 1999 under the Budapest treaty with the American Type Culture Collection (ATCC) under accession number PTA-222.

D. Sequences of Selected Identified *S. aureus* Expression Enhancing Sequences

The *S. aureus* EESs (Example 4B) in pCMOR G+1 Sa1–Sa6 were sequenced with standard methods using the luxA backprimer (LUXA-REV; SEQ ID NO:12: CCA CAC TCC TCA GAG ATG CG), and are presented below. Each sequence ends just upstream of the BamH I promoter insertion site indicated in FIG. 1 (pCMOR G+1), with the last nucleotide in each sequence corresponding to the first position in the BamH I recognition sequence (GGATCC; SEQ ID NO: 13). Note that only one of the EESs (Sa1) ended with a "G", thereby preserving the integrity of the BamH I site in the final pMK4 luxABCDE Sa1 (a.k.a. pMK4 luxABCDE P1) construct.

The vector sequence between the BamH I promoter insertion site and the ATG start codon (inclusive) of the luxABCDE cassette is as follows (SEQ ID NO:14): GGA TCC TGC AGA TGA AGC AAG AGG AGG ACT CTC T ATG. The BamH I site is indicated in bold and Gram-positive Shine-Dalgarno sequence and ATG start codon underlined.

pMK4 LuxABCDE Sa1 (SEQ ID NO:15)
ATTTATCTAAAGATGAGATTAAGC-
CAATAGAACGTCATTAGCAAAATAAAT-
TATATTGCGTCCTACAAGCAAGTT
CATGCTTATGTTTGTAGGGGGTTATTGTGGAGAA-
TAAAATTATTTCCAATAGAGAAGGGATG-
GTAATCATTTTAT
AGTGAAATATTATGAAATTGTAATAATTTAGATAT-
TGTAAAATCTAATAAGTTGTAATAATTTTAAGGGG-
TAATT ATAAAATTTGATGATACAGTATAT-
GATTTTTTTGTAATCATAATGTCAT-
CAAACATCAACCTATTATACATAATA
AAATCGTATAATGATGTAGTATTCATAAATTCGGA-
TAAAAGAATGTTAGGAAAGTTAAGCAA-
GAGGAGGATTTTA AAGTGCAAAAAAAGTAAT-
TGCAGCTATTATTGGGACAAGCGCGATT-
AGCGCTGTTGCGGCAACTCAAGCAAATG
CGGCTACAACTCACACAGTAAAACCGGGTGAAT-
CAGTGTGGGCAATTTCAAATAAGTATGG-
GATTTCGATTGCTA AATTAAAGTCATTAAA-
CAATTTAACATCTAATCTAATTTTC-
CCAAACCAAGTACTAAAAGTATCTGGCTCAAGTA
ATTCTACGAGTAATAGTAGCCGTCCAT-
CAACGAACTCAGGTGGCG

The Sa1 sequence has similarity to sequences associated with *Bacillus subtilis* LytE/papce cell wall hydrolase (Margot, et al., *J. Bact.* 180:769, (1998)).

pMK4 LuxABCDE Sa2 (SEQ ID NO:16)
AAAAAATGAGGGGTGAGACGTGAAAN-
TAAAGAAACATAACGTAGAGAAGCAAT-
CAGCCACCAAATTGATAGCAAT
CCCNTTCATCACAGACCATGAACTAAGCGACTTA-
TTTCAAAGTGAGTATACAAACAAT-
TCGTTTAGATCGCACTT
ATTTAAACATACCAGAATTAAGAAGCGTATTAAA-
TTAGTTGCTGAAAAGAATTATGAC-
CAAATAAGTTCTATTGA AGAACAAGAATTTATTG-
GTGATTTGATTCAAGTCAATCCAAATGT-
TAAAGCGCAATCAATTTTAGATATTACATC
GGATTCTGTTTTTCATAAAACTGGAATTGCGCGT-
GGTCATGTGCTGTTTGCTCAGGCAAAT-
TCGTTATGTGTTGC GCTAATTAAGCAACCAA-
CAGTTTTAACTCATGAGAGTAGCAT-
TCAATTTATTGAAAAAGTAAAATTAAATGATAC
GGTAAGAGCAGAAGCACGAGTTGTAAAT-
CAAACTGCAAAACATTATTACGTCGAAG-
TAAAGTCATATGTTAAACA
TACATTAGTTTTCAAAGGAAATTTTAAAATGTTT-
TATGATAAGCGAGGATAAAATTATGGT-
TAAATTAGCAATTG ATATGATGGGTGGCGACAAT-
GCGCCTGATATCGTATTAGAAGCCGTA-
CAAAAGGCTGTTGAAGACTTTAAA

The Sa2 sequence has limited similarity to sequences associated with the Y1pC protein from *Bacillus subtilis* (Accession numbers emb CAA74247; Y13937; gi 2633960), as well as to sequences associated with the putative P1sX protein of *Bacillus subtilis* (Accession numbers emb CAA74248; Y13937).

pMK4 LuxABCDE Sa3 (SEQ ID NO:17)

GATGGGTAAGAAGAAAATNCGGCAT-
CAGGGGNCATTNGCCATTCAGGNTGG-
GAACTGTTGGAAGGGCGTCGGGCG
GCCTTTTCGNTATTCGCAGCTGC-
GAAANGGGATGTGCTGAAGGCGAT-
TAAGTTGGGTAACGCCAGGGTTTCCAG
TCANGCGTTGTAAACGGCGGCCAGT-
GAATTCCCGGGGATCAAGCCGTTTAAG-
TATTACGACCAGTTTATATCATT
CATGGTAAAGGACAGGGCCTTCAAAAAGGTGTA-
CAACAACATT-
TGAAAAGCATAAAGTGTTAGTGACTTAGAGGT
GGTATGCCAAGGAAGGTGGATTTGGCGT-
TACCGTTGCAACACTAAAATAAAT-
TATAATTTGATAAATTAAATAGC
TGCAGTTAAAATAATGTAAAGCAACAAGAATAC-
ATTTCAAACATGTTATTTGAAATAAG-
CATAAAAATTGAGCAA ATAGAAATACATGAAG-
CATGTTATCTGATATAATTTGAACAT-
CATAATAATAATTAAGGAGGATTGGCATTTATG
GCAATCGTAAAAGTAACAGATGCA-
GATTTTGATTCAAAAGTAGAATCTGGTG-
TACAACTAGTAGATTTTTGGGCA ACATGGTGTG-
GTCCATGTAAAAT

The Sa3 sequence has similarity to sequences associated with *Staphylococcus aureus* thioredoxin (Accession numbers emb CAA11404; AJ223480).

pMK4 LuxABCDE Sa4 (SEQ ID NO:18)

GATGTATATTCACGGGGCACATGCTGC-
CGAAAAGCATCACCATTAGCTGCAATGT-
CATTACTATTGGGACGGTTT
TTATATTTTATTGCTACTCAAGGTTTTGTAAATAT-
GCAATTAATCGGTGCGATTATCTTTG-
TATTAATTACAGGT CCTCTTTTCAAGTCATATGAT-
TATGAAAGCAGCATATAATAT-
TAAAACGCCTTATACTAAAAAGACTAAAGCGAT
GAAATTTCGGAAGACTTAAAAGCN-
CAAAATTGTAGATTATATAACAAAAT-
CATGAATATAAATCAACAACAAACA
GCAGTAAGATGATTCCAAATTAGGAATGATTTTA-
CTGCTGTTTTCTTTTGACATTGTTAC-
CTCTTTTTCAATGAT TTTTTCTTTGACTACAGAT-
TCGCCCTATCTACATATATCTCTT-
TAATTTAATTGCCTTTCATGTCGTTATGTATT
ATGATAATAATAATTATAAATCGTAAC-
GATTACGTTTAAAAAGAGAGAGGTTT-
TATTATGCATTGGACAATTAT
CGGCGGTGGCATACAGGGAACTGCAATCGCACA-
AAAACTATTATCAAGCGGATTAACAACA-
GACCGATTAACAAT CATTGACCCACAC-
GAAACTTTTTGCCAAAGGTTTAACT-
CATATACAAATCGAATAGAAATGCCTTATTTAA

The Sa4 sequence has similarity to sequences associated with *Staphylococcus aureus* MnhG (Accession numbers dbj BAA35101; AB015981).

pMK4 LuxABCDE Sa5 (SEQ ID NO:19)

NACCAGNNAAAATGGTAATAAAATG-
GCAGAAGNAATAAAAAAAGGATAAA-
GAGATCCCAAACGGTATAGAGCTT
AGTATAAAATTTTCGGA-
CAATAAAATAAATACGGGTTNAAC-
CNAATTTTAACGGGAAAGCACTTCAGAATATGGT
GTGTTTGATCAAGAATAAAATTAATGAT-
GAAAATTTAACGGAGAATAGTGTATAT-
TGAGTAGATCAAGAATAAAA
AGATAATTCTACTATTGTTGTGAAGGCAAATAAG-
TAGAAGATTTTAAGTGTAATTTCTGGT-
GATTTAAATAATAA TATAAATGGAAGTACT-
GATATAAAACTTTTTAACCTACTAGAT-
TCTTATAATTTGCTTTCCATTTTATGACGATT
TTTACTCAATTGAGTGATAGAAT-
CAAAAAAGCCATCTCAAAAATTAAT-
CAAGCAAACAACATTCCAAACAATGCT
CGCAAATCACCAATGTATCACTCTC-
CAATTACGTAACTATGATTTAATTTAAG-
CATAGTTATTGAGGTTTTGTGA
TATATAGTATAAAATTAATGAGAATTAAATTTAATA-
ATGTAAAATTCATCTTCGGGGTCGGGTG-
TAATTCCCAAC CGGCAGTAAATAAAGCCTGC-
GACCTGCTAGTATGTATCATATTAGTGGCT pMK4 LuxABCDE Sa6 (SEQ ID NO:20)

CGGAAGAACGCTTTGAAGNT-
TAAGCTAATTACATCTCATCATATG-
CACGGAGATCCTTAAATGCCNAATTGAAAG
ATATTTATATGAATCATCGAGNCNGTCT-
TGATGTAGCTATTGCNAGCAGAT-
GATATTTGTCCAGCAATAACTAAT
GGGGAACAAGTGAAAGGCCTTTACCTTTATGGT-
CCATTTGGGCAGGTAAATCTTTTAT-
TCTAGGTGCAATTGCGG
AATCAGCTCAAATCTAAGAAGGTACGTTCGACA-
ATTATTTATTTACCGGGAATTTATTA-
GAACATTAAAAGGTGG CTTTAAAGATGGT-
TCTTTTGAAAAGAAATTACATCGCGTAA-
GAGAAGCAAACATTTTAATWCTTGATGATATTGG
GGCTGAAGAAGTGACTCCATGGGT-
GAGAGATGAGGTAATTGGACCTTTGCTA-
CATTATCGAATGGTTCATGAATT
ACCAACATTCTTTAGTTCTAATTTTGACTATAGTG-
AATTGGAACATCATTTAGCGAT-
GACTCGTGATGGTGAAGA
GAAGACTAAAGCAGCACGTATTATTGAACGTGT-
CAAATCTTTGTCAACACCATACTTTTTATCAGGA-
GAAAATTT
CAGAAACAATTGAATTTTAAAATGATTGGTGTA-
TAATGAATACAAATCTAAATCGTT-
TAAATGATTGAAGACAAG AT

The Sa6 sequence has similarity to sequences associated with *Bacillus subtilis* DnaI Bacsu Primosomal Protein (Accession numbers sp P06567; gi 279708).

The results discussed above indicate that RFEESS is a useful method for the isolation of EESs effective to result in bioluminescence when the EESs are operably linked to luciferase genes. Furthermore, the data provide examples of specific *S. aureus* EESs effective to produce such bioluminescence

EXAMPLE 5

Evaluation of Aldehyde Toxicity in Animals

Four mice were injected IP at 0, 2, 4 and 6 hr with 500 µl volumes of n-decyl aldehyde at concentrations of 0.1% and 0.01%. Aldehyde solutions were prepared as follows: 100 µl of aldehyde was diluted in 900 µl of ethanol. 10 µl of this 10% solution was then diluted into 990 µl of sterile phosphate buffered saline (PBS) pH 7.4 to give a 0.1% final volume of aldehyde solution. The animals were observed over a 24-hour period. None of the mice showed any apparent symptoms of illness or abnormal behavior after 24 hrs.

EXAMPLE 6

Evaluation of pMK4 LuxAB Sa3 in *S. aureus* for Bioluminescence in Mice

Twenty four hours after initial injections, the four mice tested as described in Example 5 were injected with a pathogenic strain (8325-4) and a clinical methacillin-resistant (MRSA) strain of *S. aureus* containing pMK4 luxAB Sa3. The *S. aureus* strains were grown to an O.D (600 nm) of approximately 0.5 in 10 ml. volumes of LB containing 5 µg/ml chloramphenicol. The bacteria were pelleted and each sample resuspended in 10 mls. of sterile PBS. The O.D of the samples was re-measured and adjusted to give $1 \times 10^5$, $1 \times 10^6$, and $1 \times 10^7$ cells per ml. using the conversion: # of cells=$(A600)(11.1 \times 10^8)$. The dilutions were confirmed by plating on chocolate plates containing 5 µg/ml chloramphenicol.

Doses were either 250 µl intra-peritoneal (IP; $1 \times 10^5$ and $1 \times 10^6$ per ml.) or 100 µl intramuscular (IM; in the thigh with $1 \times 10^6$ and $1 \times 10^7$ per ml.). The four mice were then injected IP with 500 µl of 0.1% n-decyl aldehyde. This administration of aldehyde was repeated at 2, 4 and 6 hrs just prior to imaging for bioluminescence. Immediately prior to imaging, the mice were anesthetized by intramuscular (IM) injection with a 4:1 mixture of "Ketaset" (Ketamine [Fort Dodge Products]) at 100 mg/ml and "Rompumn" (Xylazine small animal [Darby Drug Company]) at 20 mg/ml, at a dose of 15 µl per 10 g body weight. Accordingly, a 20 g mouse received 30 µl. The anesthesia typically took effect in 2–3 minutes, and the animals typically remained sedated for 20–30 minutes. If necessary, a second dose of 7 µl per 10 g of body weight was administered. In general, the animals recovered 60–90 minutes following administration of a single dose. Animals which had been dosed twice, however, could take as long as 4 hours to recover.

The mice were imaged essentially as described in Contag, et al., U.S. Pat. No. 5,650,135. Bioluminescence was observed at 0 hr. and at 2 hr, indicating that exogenously-administered aldehyde may be used in vivo to image cells transformed only with luxA and luxB. These results demonstrate that the exogenously-administered aldehyde can diffuse throughout the body, since an IP injection of aldehyde enables the generation of light from luxAB bacteria located in the thigh muscle.

EXAMPLE 7

Evaluation of pMK4 luxABCD Sa2 (pCMOR G+1 Sa2) in *S. aureus* for Bioluninescence in Mice

*S. aureus* strains 8325-4 and MRSA containing pCMOR G+1 Sa2 (pMK4 LuxABCDE Sa2; pXEN-lux-1) were prepared as described in Example 6 and tested for bioluminescence in mice. The strains were inoculated into mice at 100 µl IP ($4 \times 10^6$ per ml.) and 100 µl IM ($4 \times 10^6$ per ml. in right thigh and $4 \times 10^7$ per ml. in left thigh) and monitored at time 0, 4, 6 and 24 hr. The mice were then imaged as described above at times 0, 4 hr, 6 hr, and 24 hr. Both strains were readily visualized in the animals in vivo.

EXAMPLE 8

Construction of the pDL289 LuxABCDE (pCMOR G+2) Shuttle Vector, and Evaluation of its Bioluminescent Properties in *Streptococcus pneumoniae*

A. Construction of pDL289 LuxABCDE Shuttle Vector

The luxABCDE cassette generated as described in Example 3 was isolated from pSK⁻luxABCDE via a BamH I/Sal I digest and cloned into the BamH I/Xho I sites of the Gram-positive/negative shuttle vector pDL289 (Buckley, N., et al., (1995) *J. Bacteriol* 177:5028–5034, incorporated herein by reference), generating pDL289 luxABCDE (pCMOR G+2). As was the case in Example 3, the cloning was carried out so that a BamHI restriction site was maintained upstream of the luxA coding region, but in this case, the luxABCDE cassette was in the same orientation as, and downstream of, the lacZ promoter. pCMOR G+2 was then electroporated into *E. coli* DH5α. The resulting positive clones were extremely bright (since the cassette was downstream of lacZ promoter), with a pure culture allowing the camera to reach a sensitivity of 4.0.

B. Random Fragment Expression Enhancing Sequence Screen (RFEESS) Using pDL289 LuxABCDE (pCMOR G+2)

One of positive clones identified in part (A), above, was plasmid-prepped and the resulting DNA was used to build a promoter library that could be screened in *S. pneumoniae*. Genomic DNA from *Streptococcus pneumoniae* R6 was cut with Sau3A in a partial digest (Ausubel, F. M., et al., *Current Protocols in Molecular Biology*, John Wiley and Sons, Inc., Media, Pa. (1995)) and ligated with the pCMOR G+2 plasmid cut with BamHI. These ligations were then electroporated into *E. coli* DH5α. The resulting transformants were pooled directly from plates, their plasmid DNA extracted, and this DNA electroporated into competent cells of a pathogenic encapsulated strain of *Streptococcus pneumoniae*.

Approximately 20,000 Gram-positive transformants on chocolate plates containing 250 µg/ml kanamycin were then screened for bioluminescence using a photon counting CCD camera (Hamamatsu Photonics, model 2400-32) as described above. Eighty medium to high light intensity colonies were picked and the 21 brightest of these streaked for single colonies. These 21 isolates were monitored for light intensity readings at both 24 and 72 hrs on chocolate plates containing 400 µg/ml kanamycin. At 24 hr., individual colonies were less than about 0.5 mm in diameter, with light being emitted from the entire streak. By 72 hr however, the single colonies had grown to a size comparable to than achieved by *E. coli* growing for 16 hr., and were strongly bioluminescent, with very little to no light being emitted from the solid streak. Light intensities were also measured from 16 hr liquid cultures of BHI containing 250 µg/ml kanamycin (O.D. 0.5–0.8). Bit Range Light Units (BRLUs) are equal to the rate of bit range change (expressed as bit range per second) on a Hamamatsu Photonics model 2400-32 intensified CCD camera connected to an Argus Image Processor set at a gain of "zero". A summary of this information is shown in Table 3, below:

TABLE 3

| Isolate | Light Intensity (BRLU/second) | | | c.f.u. at inoculation | c.f.u. from animals |
|---|---|---|---|---|---|
| | Plate - 24 hr | Plate - 72 hr | Solution - 16 h | | |
| Sp1 | 9.85 | 8.53 | 9.31 | $1.7 \times 10^6$ | |
| Sp2 | 7.64 | 13.84 | 1.12 | | |
| Sp3* | 0.70 | 1.10 | 1.42 | | |
| Sp4 | 4.34 | 5.82 | 2.61 | | |
| Sp5 | 5.45 | 9.48 | 12.19 | $3.2 \times 10^5$ | |
| Sp6 | 6.74 | 9.48 | 20.08 | $6.1 \times 10^5$ | |
| Sp7 | 6.74 | 8.00 | 2.25 | | |
| Sp8 | 5.33 | 6.40 | 1.60 | | |
| Sp9 | 7.31 | 16.00 | 12.19 | $3.4 \times 10^6$ | ~0 |
| Sp10 | 3.88 | 7.76 | 2.56 | | |
| Sp11 | 7.31 | 8.83 | 1.42 | | |
| Sp12 | 4.00 | 5.33 | 8.00 | | |
| Sp13 | 7.11 | 6.24 | 2.13 | | |
| Sp14 | 17.36 | 13.13 | 11.38 | | |
| Sp15 | 6.10 | 14.63 | 5.12 | | |
| Sp16 | 8.83 | 15.06 | 23.27 | $5.8 \times 10^5$ | $2.5 \times 10^5$ |
| Sp17 | 5.82 | 7.11 | 10.89 | | |
| Sp18 | 3.76 | 8.83 | 0.91 | | |
| Sp19 | 7.53 | 13.47 | 1.68 | | |
| Sp20 | Not measured | Not measured | <0.27 | | |
| Sp21 | 7.53 | Not measured | Not measured | | |

*Isolate Sp3 did not give a zone of haemolysis on chocolate plates containing 250 μg/ml kanamycin.

C. Sequences of Selected Identified S. pneumoniae Expression Enhancing Sequences The S. pneumoniae EESs in pDL289 luxABCDE Sp1, 5, 6, 9, 16 and 17 were sequenced with standard methods using the luxA backprimer (LUXA-REV; SEQ ID NO:12), and are presented below. Each sequence ends just upstream of the BamH I promoter insertion site, with the last nucleotide in each sequence corresponding to the first position in the BamH I recognition sequence (GGATCC; SEQ ID NO:13). Note that only two of the EESs (Sp9 and Sp16) ended with a "G", thereby preserving the integrity of the BamH I site in the final pDL289 luxABCDE Sp9 and pDL289 luxABCDE Sp16 constructs.

The vector sequence between the BamH I promoter insertion site and the ATG start codon (inclusive) of the luxABCDE cassette is as follows (SEQ ID NO:14): GGA TCC TGC AGA TGA AGC AAG AGG AGG ACT CTC T ATG. The BamH I site is indicated in bold and Gram-positive Shine-Dalgarno sequence and ATG start codon underlined.

pDL289 LuxABCDE Sp1 (SEQ ID NO:21)
AGGACGNTAGGACGTGACGAGCCGAAAG-GCTTNAGCGTTCGAGCCGACACGGA-CAAAGGACGCCGCCCTTGGTTA CTTGTTGTCAATTAGACCATGNAATAAAGTAAG-CGGACATGGTATAATAGNTAGGTCG-CAACGTTCTTTCGCTAA GTTACGAACTTAGATTG-GAGGTGAGCGCCCAATACGCAAACCGC-CTCTCCCCGCGCGTTGCCGATTCATTAATGC AGCTGGCACGACAGGTTTCCCGACTG-GAAAGCGGGCAGTGAGCGCAACGCAAT-TAATGTGAGTTAGCTCACTCAT TAGGCACCCCAGGCTTTACACTTTATGCTTCCG-GCTCGTATGTTGTGTGGAATTGTGAGCG-GATAACAATTTCAC ACAGGAAACAGCTATGAC-CATGATTACGCCAAGCTATTTAGGTGA-CACTATAGAATACTCAAGCTATGCATCCAA CGCGTTGGGAGCTCTCCGGATCAGGT-CATTCGAGTTACCGATTTATCACATA-GATGATATGGTAAGATTCAGTTA GAAGAAAGAGTCACAAACACACTTTGTGGCT-TTTTTATTTCCATAAAAATGGTAAAAT-AGTAGGAGTAGAAATGG AGTTCGAGACAT-GAAAGTAATA

The Sp1 sequence has similarity to sequences associated with Streptococcus pneumoniae D-glutamic acid adding enzyme MurD (murD), undecaprenyl-PP-MurNAc-pentapeptide-UDPGlcNAc GlcNAc transferase (murG), cell division protein DivIB (divIB), orotidine-5'-decarboxylase PyrF (pyrF) (Massidda, O., et al., Microbiology 144 (11) :3069–3078 (1998); Accession number gb|AF068902).

pDL289 LuxABCDE Sp5 (SEQ ID NO:22)
AGACAAAGAACGTCCGCCCTTGGTACT-TGTTGTCAAATTAGACCATGGAATAAAG-TAAGCGGACATGGTATAATA GCTAGGTCGCAACGTTCTTTCGCTAAGTTACGAA-CTTAGATTGNAGGTGAGCGCCCAATACG-CAAACCGCCTCTC CCCGCGCGTTGGCCGA-TTCATTAATGCAGCTGGCACGACAGGTTTCCC-GACTGGAAAGCGGGCAGTGAGCGCA-AC GCAATTAATGTGAGTTAGCTCACTCATT-AGGCACCCCAGGCTTTACACTTTATGCT-TCCGGCTCGTATGTGTGTT GGAATTGTGAGCGGATAACAATTTCACACAGGA-AACAGCTATGACCATGATTACGCCAA-GCTATTTAGGTGACAC TATAGAATACTCAAGC-TATGCATCCAACGCGTTGGGAGCTCTC-CGGATCGTCTGCCAGGTTCAGCAACACGCCCA CATCCGGGCGCAAGTGGCTGGACCAATG-CAACTGGAAAGAAGAGAGCTCGGCGCA-GAGAACGTCGAGGCGAGGGG TGGCCGTGAGGGCGTCGAAAAGCGAAACGCCG-ATATTGCCCACCGCCAGTGCGCGCTTGC-CGGTGCGCTTGGCAT CTGCCTGCAT

The Sp5 sequence has similarity to sequences associated with Mycobacterium tuberculosis UDP-N-acetylmuramoylalanine—D-glutamate ligase (UDP-N-acetylmuranoyl-L-alanyl-D-glutamate synthetase; D-glutamic acid adding enzyme) (Accession numbers sp|O06222; MURD_MYCTU).

pDL289 LuxABCDE Sp6 (SEQ ID NO:23)
ATGCTTCCGGGNTCGTATGTTGTGTG-GAATTGTGAGCGGAATACCAATTTCACA-CAGGAAACAGCTATGACCATG

ATTACGCCAAGCTTATTTAGGTGACACTATAGA-
ATACTCAAGCTATGCATCCAACGCGTTGGGAGCT-
CTCCGGAT CAAAATGACAATCGGCAGCATGT-
GCGGGATGGATTATGCGAGTCGGA-
CATCTTGCCTAGGACGCGCCCCAACTGG
GAGCAGCCCTTCATCAAGGAGTACAGCAAATCA-
TTGCCGCTGCGCGGCATGAACTCGTGGGCTTCAA-
AGCTTGCC CACATCTTCTTGCGGGCAAAGATAC-
CGGCAATACCGAGGATGAGGACCAC-
TAGCGAGATAAGGAAAGGAACGTTG
AGCCCGTGCCAGAGGGCAAGGTGCGAATGATG-
CTCCAATCCCACGGCAGCCACTGCATCATCGATC-
GGGGCATCA AAGAGCCCGAGCACAAATAC-
CAGCGGCAGAGACATAAAGCCCG-
GCAAAGCTGCAGGTAGCCACAGCGACACTGGT
GCTTCATGGACATCTCCCATGTCGCGAG-
GTCCGTCAAAGAAGGCCCGAAGA-
CAATCTTTGCCCAGTAAGTAAAG GTGAAGAACG-
CACCGATACCGGCAAC pDL289 LuxABCDE Sp9 (SEQ ID NO:24)
GCAAGGCCTTGAGTAGCTTTATCCA-
GACTGAAGGCCCGCTATCTTTGGAAG-
GCAGGATATAAAGAAGATTCTCT
TGCAGAGCGGGCGGAACGAGTAGGCTATGTG-
CTGCAAAATCCCAATCAAATGATTTCAACCAAT-
ATGATTTTTGA TGAGGTGGCTCTGGGACTC-
CGTTTGCGAGGTGTGGACGAGCAG-
GAAATTGAAACGAGAGTCTATGAAACCTTGAA
AATCTGTGGTCTCTATGAATTCCGTAAT-
TGGCCCATTTCTGCCCTGTCATTTGGT-
CAGAAAAAACGTGTGACTAT
TGCCTCAATTTTGGTCTTAGGCGCTGAAATTATC-
CTCCTAGATGAACCGACTGCGGGTCAAGACCAG-
AAGAACTA TACTGAGATTATGGAATTTCTCGAA-
GAACTGCATCAACAAGGGCATACCAT-
TGTCATGATTACCCATGATATGCA
ATTGATGCTGGATTATTCAGATCGAGCCCTTGTC-
ATGGTGGATGGGGAATTGATTGCT-
GATACTGATCCAGCTAG TCTGTTGAGCAATCCT-
GAGCTGTTAGTAAAAGCCAACCTAAAA-
GAGACTTCTATCTTCAACTTGGCTAAGAAACT
CGACGTG

The Sp9 sequence has similarity to sequences associated with *Methanococcus jannaschii* cobalt transport ATP-binding protein O homolog (Accession numbers gi|1591732 and U67551).

pDL289 LuxABCDE Sp16 (SEQ ID NO:25)
TGAATGTTCGGTACGCACCAGTCT-
TCGTCTGCTCTCAAGGACGTGGACAT-
TCATGATGGATTTGCCACTACGAAG
ATGACCTAAGTCAGTNCAAGAAGAAATTATTAA-
GAAAAATAAAGGTGAAGACTTAATC-
CGTCCTCACTCTAGAAG
GAAGTCACTTAGTGGCTTCCTTTTGTCTTTAGA-
AAATACCTCTAAATATGGTAAAATAGTAGAAGA-
ATAATGTGA GGAAAATGAATGTCAAAT-
AGTTTTGAAATTTTGATGAATCAAT-
TGGGGATGCCTGCTGAAATGAGACAGGCTCCT
GCTTTAGCACAGGCCAATATTGAGC-
GAGTTGTGGTTCATAAAATTAGTAAGG-
TATGGGAGTTTCATTTCGTATTT
TCTAATATTTTACCGATTGAAATCTTTTTAGAAT-
TAAAGAAAGGTTTGAGCGAA-
GAATTTTCTAAGACAGGCAAT
AAAGCTGTTTTTGAAATTAAGGCTCGGTCTCAA-
GAATTTTCAAATCAGCTCTTGCAGTCCTACTATA-
GGGAGGCT TTCTCTGAAGGTCCATGTGCTAGT-
CAAGGTTTTAAGTCCCTTTAT-
CAAAATTTGCAAGTTCGTGCTGAGGGTAAT
CAGCTATTTATTGAAG

The Sp16 sequence has similarity to sequences associated with *Bacillus subtilis* DNA polymerase III alpha chain (Accession numbers gi|1591732 and U67551) and *Staphylococcus aureus* DNA polymerase III (Accession numbers dbj|BAA13160; D86727).

pDL289 LuxABCDE Sp17 (SEQ ID NO:26)
TGAAAAAGCAGGGCTATGTGAAGCGCTG-
GCGCCGANCCCCGATGATGAGCGTCG-
CACCCTCGCTGCCCTGACTGC
NGACGGCGCCTCCCTCCGCACCCGCOCCGAATG-
CATCCCCGAAGCCATGGCCAAGGC-
CTATAAGGAGGTAGGCCT
CGACCTTGCCGAGTTCAAGAAATCGCTGACATC-
CTGGCCCGGCGTGCCTGTGGACGTG-
GAGCTGCCGTGGCCATCT
GGGGATGACTTTGTGGGTTAAAGTGTGGCCTTC-
ATATAGCAGATGAGGACGGCTATACTGGCTTA-
AGAGTTTTGA CTCTATTTACGTAAAATTTTTTCA-
CACTATGAGAGGAGGGGCCATGGCTA-
CAGCAGTAGACGTCGCGCAGGTTAT
CTACAACAAACTGGGGTGGGTCGATGCGTGGA-
AGCTGGAGAAGCTTACGTATTACTGC-
CAAGCGTGGAGCCTGGG CTGGTACGGGCGAC-
CTCTTGTCTCGAATGAATTTCAGGCGTG-
GAAGGACGGTCCGGTTGAACCCGACCTCTATCG
CGAGAATAAATATCAACGCTC-
CGAGAAATCCTCCACGGTGTTACCGG-
GAGCTGATGTAGAGGCTATAGGGGAGGA AGC-
CGAAAA

EXAMPLE 9

Evaluation of *S. pneumoniae* Transformed With pDL289 LuxABCDE Sp1, 5, 6, 9 and 16 for Bioluninescence in Mice The 16 hr liquid cultures of *S. pneumoniae* containing pDL289 luxABCDE Sp1, 5, 6, 9 and 16 were tested in mice. Bacteria from 1 ml. of each culture were pelleted, resuspended in 1 ml. PBS, and 100 μl of this and a 1/10 dilution were inoculated into the left and right thigh muscles of a mouse, respectively. The lower of each dilution was plated on chocolate agar containing 250 μg/ml kanamycin to assess colony forming units (c.f.u. at innoculation; see Table 3, above). Each of the mice was monitored at time 0, 4, 7 and 24 hr for 5 min periods under the CCD camera.

As is evident from the data in Table 3, *S. pneumoniae* containing pDL289 luxABCDE Sp1, 5, and 6, gave between $1 \times 10^4$ and $6 \times 10^4$ c.f.u., with >80% plasmid retention. No c.f.u. were recovered from Sp9 (probably due to ineffective grinding). Whereas Sp16 gave $2.5 \times 10^5$ c.f.u. with >90% plasmid retention.

Based on the above data, *S. pneumoniae* containing pDL289 luxABCDE Sp16 was selected as the best candidate strain for further studies.

EXAMPLE 10

Construction of Bioluminescent *Mycobacterium tuberculosis* Using pCMOR G+3 Shuttle Vector The luxABCDE cassette generated as described in Example 2 is isolated from pSK⁻luxABCDE via a BamH I/Kpn I digest and cloned into the BamH I/Kpn I sites of the Gram-positive/negative shuttle vector pSUM39 (Ainsa, et al., (1996) *Gene* 176:23–26, incorporated herein by reference), generating pSUM39 luxABCDE (pCMOR G+3). As above, the cloning is carried out so that a BamH I restriction site is maintained upstream of the luxA coding region. One of skill in the art will recognize that other Gram-positive/negative shuttle vectors suitable for use with *Mycobacterium tuberculosis*, such as pSUM 40 or pSUM 41 (Ainsa, J. A., et al., (1996) *Gene* 176:23–26), could be used instead of pSUM 39.

To identify potentially useful promoter sequences, genomic DNA from *Mycobacterium tuberculosis* is cut with Sau3A in a partial digest (Ausubel, F. M., et al., *Current Protocols in Molecular Biology*, John Wiley and Sons, Inc., Media, Pa. (1995)) as described above and ligated with pCMOR G+3 plasmid cut with BamH I. These ligations are then electroporated into *E. coli* DH5α. The resulting transformants are then pooled, their plasmid DNA extracted, and this DNA is then electroporated into competent *M. smegmartis* host cells. Transformants which have incorporated the vector are then picked, expanded, and their plasmid DNA is electroporated into competent *M. tuberculosis* host cells.

Gram-positive transformants are screened for bioluminescence using a photon counting CCD camera as described above.

EXAMPLE 11

Construction of Bioluminescent *Listeria monocytogenese* Using the pCMOR G+1 Shuttle Vector Genomic DNA from *Listeria monocytogenese* is cut with Sau3 A in a partial digest (see, e.g., Ausubel, F. M., et al., *Current Protocols in Molecular Biology*, John Wiley and Sons, Inc., Media, Pa. (1995) and ligated with pCMOR G+1 plasmid (Example 4) that had been cut with BamH I. These ligations are then electroporated into *E. coli* DH5α. The resulting transformants are pooled directly from plates, their plasmid DNA extracted, and this DNA electroporated into competent Listeria monocytogenese host cells.

Gram-positive transformants are screened for bioluminescence using a photon counting CCD camera as described above.

EXAMPLE 12

Identification of a Cross-species Gram-positive Promoter Sequence

Due to the wide host range of pMK4, a set of the pCMOR G+1 constructs containing *S. aureus* EESs (Sa1–6) were electroporated into a pathogenic strain of *Listeria monocytogenese* (ATCC 23074) to test whether any of the *S. aureus* EESs would induce light in Listeria. Although all six plasmid were successfully moved into this strain of Listeria, only pCMOR G+1 Sa4 was found to give significant levels of light, with the remainder of the constructs inducing only low levels of bioluminescence. Since pCMOR (G+1 Sa4 was able to induce high levels of light in both *S. aureus* and *L. monocytogenes*, this construct may be used to transform other genera of Gram-positive bacteria to a light phenotype.

EXAMPLE 13

Comparison of Bioluminescence From *S. aureus* Containing the Modified LuxABCDE Vs *S. aureus* Containing the Native LuxCDABE The *S. aureus* construct pCMOR Sa1 (which retained the BamH I site between the promoter and the luxABCDE cassette; see Example 4) was selected as the starting vector for comparing the levels of bioluminescence generated using the engineered luxABCDE cassette with levels of bioluminescence generated using the native luxCDABE cassette (where the two cassettes were each under the control of the *S. aureus* Sa1 promoter). The luxCDABE construct was generated as follows: The native luxCDABE cassette was first isolated from pSB417 (Winson, et al., 1998, *FEMS*, 163:185–202) as a BamHI/SalI fragment, and this fragment was then used to replace the corresponding luxABCDE BamHI/SalI fragment dropped out of pCMOR Sa1 to generate pMK4 luxCDABE Sa1. The cloning was carried out in *E. coli* DH5α and the finished plasmid was moved into *S. aureus* RN4220.

Bioluminescence generated by the two different cassettes was compared using transformed *E. coli* DH5α and transformed *S. aureus* RN4220 cells, each containing either pCMORG+1 Sa1 (pMK4 luxABCDE Sa1) or pMK4 lux-CDABE Sa1. Exponential cultures of each of the four bacterial strains were diluted across black 96-well microtitre plates in doubling dilutions (~0.3 log) and monitored for light over a period of 30 min at 37° C. using a photon counting CCD camera (Hamamatsu, model 2400-32). The contents of each well were then plated to allow the number of colony forming units (CFU) to be compared to levels of bioluminescence (relative light units; RLU).

Figure 2:
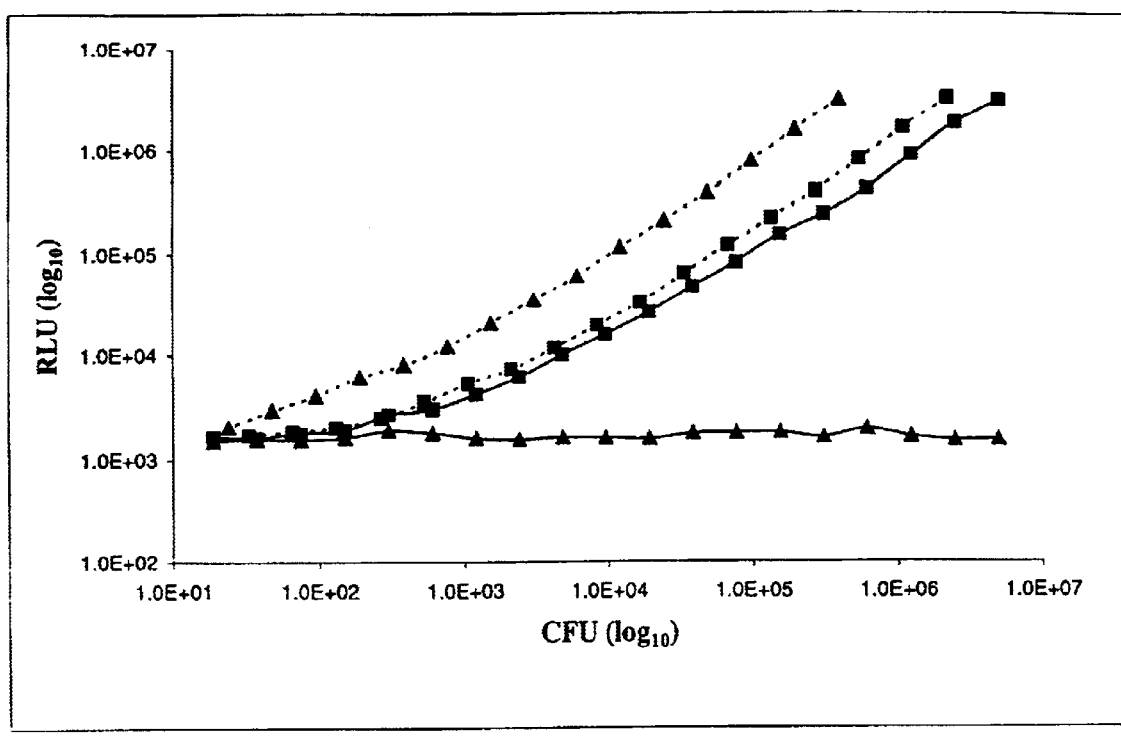
FIG. 2 is a comparison of bioluminescence from S. aureus and E. coli containing the native luxCDABE vs the modified luxABCDE. Exponential cultures of S. aureus RN4220 pCMOR (-■-), S. aureus RN4220 pMK4 luxCDABE Sa1 (-▲-), E. coli DH5α pCMOR Sa1 (..■..) and E. coli DH5α pMK4 luxCDABE Sa1 (..▲..) were diluted across black 96-well microtitre plates in doubling dilutions (−0.3 log) and monitored for light over a period of 30 min using a photon counting CCD camera (Hamamatsu, model 2400-32). The contents of each well was then plated to allow the number of colony forming units (CFU) to be compared to levels of bioluminescence (RLU). pCMOR Sa1 is also known as pMK4 luxABCDE P1.
Figure 3:
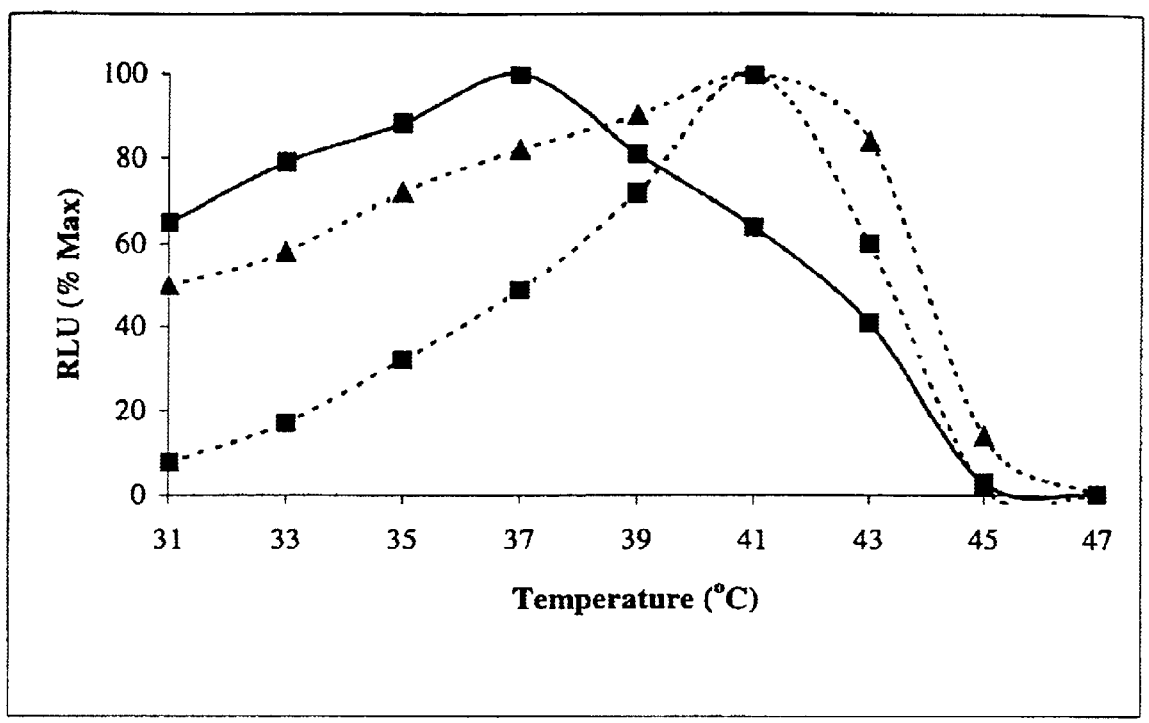
FIG. 3 is a plot showing the temperature stability of the modified luxABCDE. Exponential cultures of S. aureus RN4220 pCMOR Sa1 (-■-), E. coli DH5α pCMOR Sa1 (..■..) and E. coli DH5α pMK4 luxCDABE Sa1 (..▲..) were grown to approximately $10^7$ c.f.u/ml at 30° C. and 1 ml. volumes of each placed in heating blocks set at 31, 33, 35, 37, 39, 41, 43, 45 and 47° C. After 1 hour at each of these elevated temperatures, the 9 heating blocks were sequentially placed inside the chamber of a photon counting CCD camera (Hamamatsu, model 2400-32) and light from each of the three cultures recorded for a period of 1 min. Shown are the RLU at each of the temperatures, with this data expressed as a percentage of the maximum bioluminescence attained and adjusted for variations in the number of CFU.
Figure 4:
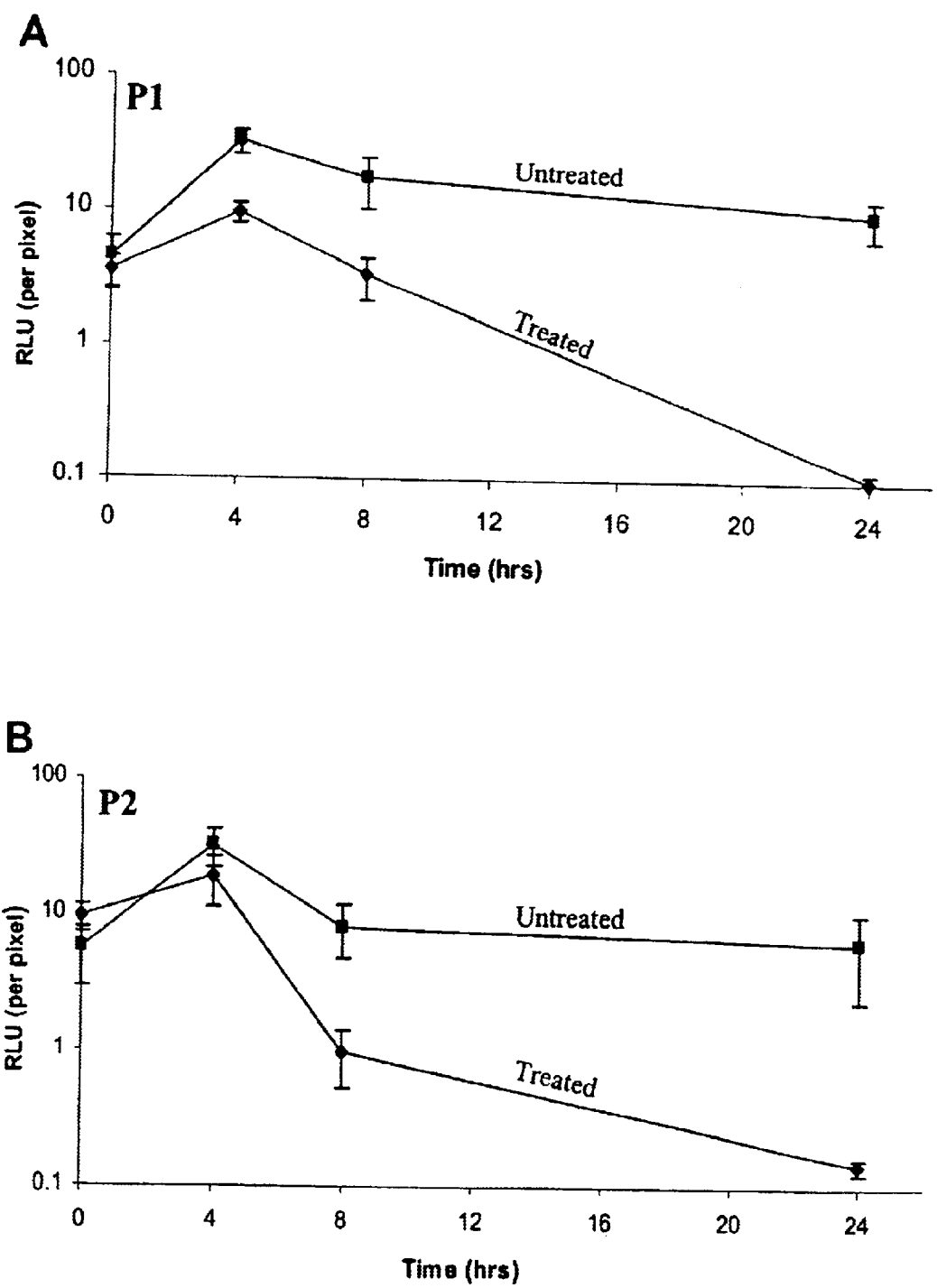
FIG. 4, panels A and B, are graphs depicting bioluminescence data recorded from S. aureus 8325-2 pMK4 luxABCDE P1-(panel A) and S. aureus 8325-4 pMK4 luxABCDE P2-(panel B) infected mice. Each data set represents the mean number of RLU from six mice either untreated (■) or treated (▲) with amoxicillin (10 mg/kg), imaged both dorsally and ventrally for 5 minutes at 0, 4, 8, and 24 hours post-infection using an ICCD camera. Error bars depict standard errors of the means.

The results are shown in FIG. 2. Both the luxCDABE and the luxABCDE cassettes function comparably well in *E. coli*, but only luxABCDE resulted in significant bioluminescence in *S. aureus*. Sa1:luxABCDE produced approximately 4-fold less light than Sa1:luxCDABE in *E. coli*. One possible explanation for this phenomenon is that high transcription and high translation efficiencies may be energetically-costly and thus detrimental to the cell, leading to decreased bioluminescence.

The minimum number of *S. aureus* RN4220 pCMOR Sa1 detectable at 37° C. using the Hamamatsu Photonics model 2400-32 CCD camera was approximately 400 c.f.u. However, this minimum number was significantly improved upon by using a more sensitive, liquid nitrogen cooled integrating CCD camera (see Example 14, below). The MRSA strain produced significantly more light (approximately 4-fold) than either RN4220 or 8325-4, regardless of the plasmid (PCMOR Sa1–20) tested.

The results show that using the methods of the present invention, one can generate Gram-positive organisms capable of producing over $1 \times 10^4$ RLU per $1 \times 10^6$ organisms (as measured on the XEN-3 Hamamatsu Photonics model 2400-32 photon counting CCD camera).

EXAMPLE 14

Minimum Number of Bioluminescent *S. aureus* and *S. pneumoniae* and *L. monocytogenese* Detected in Liquid Culture Exponential cultures of light *S. aureus* RN4220 pCMOR G+1 Sa1, *S. pneumoniae* pCMOR G+1 Sp16 and *L. monocytogenes* ATCC23074 pCMOR G+1 Sa4 were monitored using a highly sensitive liquid nitrogen cooled integrating CCD camera (Princeton Instruments, Trenton, N.J.; model LN/CCD 1340-1300-EB/1) to determine the minimum number of c.f.u detectable of each of these strains of bacteria. Cultures were diluted across black 96-well microtitre plates from bacterial concentrations of approximately $10^3$/well to $10^1$/well in doubling dilutions (~0.3 log) and monitored for light over a period of 10 min. As few as 80 c.f.u of both *S.*

*aureus* and *S. pneumoniae* could be detected at 37° C. using the Princeton Instruments camera, whereas approximately 400 c.f.u of *L. monocytogenes* were detectable by this same method.

EXAMPLE 15

Temperature Stability of Bioluminescence in *S. aureus*

To monitor pathogenic bacteria from within animals using bioluminescence (Contag, C., et al., (1995) *Mol. Microbiol.* 18:593–603), it is important that both the lux genes and Lux proteins function adequately at body temperature (i.e., around 37° C). In order to determine whether modifying the lux genes had altered the temperature range over which bioluminescence occurs optimally in bacterial cells, light arising from the modified luxABCDE cassette was compared to that from the native LuxCDABE in both Gram-negative and Gram-positive bacteria between 31° C. and 47° C. Since *S. aureus* RN4220 pMK4 luxCDABE Sa1 was previously shown to be dark (FIG. 2), only *S. aureus* RN4220 pCMOR G+1 Sa1, *E. coli* DH5α pCMOR G+1 Sa1 and *E. coli* DH5α pMK4 luxCDABE Sa1 were tested in this set of experiments. Exponential cultures of the latter three bacterial strains were grown to approximately $10^7$ c.f.u/ml at 30° C. and 1 ml. volumes of each placed in heating blocks set at 31, 33, 35, 37, 39, 41, 43, 45 and 47° C. After allowing the bacteria to acclimatize and grow at each of the elevated temperatures for a period of 1 hour, the 9 heating blocks were sequentially placed inside the chamber of a photon counting CCD camera (Hamamatsu, model 2400-32) and light from each of the three cultures recorded for a period of 1 min. To eliminate errors in the number of relative light units arising from variations in bacterial numbers, each culture was plated to allow c.f.u. to be recorded and the light data adjusted accordingly.

As can be seen from FIG. 5, the maximum light to be recorded from a culture of *S. aureus* RN4220 pCMOR G+1 Sa1 was at 37° C. Furthermore, between 31° C. and 41° C. the light emission from this strain remained above 60% of this maximum, even at 2 and 4 hours, indicating that the Lux enzymes were stable within this narrower temperature range. In contrast, both *E. coli* DH5α pCMOR Sa1 and *E. coli* DH5α pMK4 luxCDABE Sa1 gave maximum light at 41° C., with *E. coli* DH5α pCMOR Sa1 actually being slightly brighter at this temperature.

EXAMPLE 16

Transformation and Evaluation of *Listeria monocytogenes* With Modified LuxABCDE Operons A modified luxABCDE plasmid was used to successful transform gram-positive *Listeria monocytogenes*, as described above in Example 14. The gram positive bacteria carrying a modified luxABCDE operon were highly bioluminscent and, in addition, could be monitored in vivo in animals. Plasmid loss in the absence of antibiotic selection was shown to be minimal from *L. monocytogenes* over a period of 24 to 48 hours in vivo (>80% plasmid retention) with no observable structural instability.

All of plasmids described have been deposited at Xenogen Corporation, 860 Atlantic Avenue, Alameda, Calif. 94501.

---

What is claimed is:

1. An expression cassette comprising,
a polynucleotide encoding luciferase luxA, luxB, luxC, luxD and luxE gene products arranged in the following relative order 5'-luxA-luxB-luxC-luxD-luxE-3', wherein (a) transcription of the polynucleotide results in a polycistronic RNA encoding all the gene products; (b) each of the luxA, luxB, luxC, luxD and luxE gene products is expressed as an individual polypeptide; and (c) polynucleotide sequences comprising Gram-positive ribosome-binding site sequences are located 5' to all of said lux coding sequences and further wherein the lux gene products are obtained from Gram-negative bacteria having a naturally occurring lux operon ordered luxCDABE.

2. The expression cassette of claim 1, further comprising a multiple-insertion site located 5' to said luxA, luxB, luxC, luxD and luxE coding sequences.

3. The expression cassette of claim 1, wherein at least one Gram-positive ribosome binding site comprises the sequence presented as SEQ ID NO:1.

4. The expression cassette of claim 1, wherein the coding sequences of the gene products are derived from *Photorhabdus luminescens*.

5. The expression cassette of claim 1, wherein the polynucleotide further comprises a promoter located 5' to all of said lux coding sequences wherein transcription of the polynucleotide results in a polycistronic RNA encoding all the lux gene products.

6. The expression cassette of claim 5, wherein said promoter is contained in an Expression Enhancing Sequence-selected from the group consisting of Sa1 (SEQ ID NO:15), Sa2 (SEQ ID NO:16), Sa3 (SEQ ID NO:17), Sa4 (SEQ ID NO:18), Sa5 (SEQ ID NO:19), and Sa6 (SEQ ID NO:20).

7. The expression cassette of claim 5, wherein said promoter is contained in an Expression Enhancing Sequence selected from the group consisting of Sp1 (SEQ ID NO:21), Sp5 (SEQ ID NO:22), Sp6 (SEQ ID NO:23), Sp9 (SEQ ID NO:24), Sp16 (SEQ ID NO:25) and Sp17 (SEQ ID NO:26).

8. The expression cassette of claim 7, wherein said promoter is contained in Expression Enhancing Sequence Sp16 (SEQ ID NO:25).

9. The expression cassette of claim 1, wherein the expression cassette is contained within a bacterial transposon.

10. The expression cassette of claim 1, wherein the expression cassette is contained within a bacterial mini-transposon.

11. The expression cassette of claim 1, wherein the coding sequences of the gene products comprise codons that are optimal for expression of the gene products in a host system into which the expression cassette is to be introduced.

12. A shuttle vector comprising:
an expression cassette according to claim 1;
a polynucleotide encoding a selectable marker;
a Gram-positive origin of replication; and
a Gram-negative origin of replication.

13. A method of modifying a Gram-positive bacterium to produce light, comprising transforming the Gram-positive bacterium with an expression cassette according to claim 1.

14. A method of screening an analyte for its ability to affect expression of a reporter marker, comprising:
providing the analyte to Gram-positive bacteria comprising the luciferase expression cassette of claim 1, wherein said reporter marker comprises luciferase; and
monitoring the effect of the analyte on the ability of the Gram-positive bacteria to produce light, thereby identifying whether the analyte affects expression of the reporter in Gram-positive bacteria.

15. A Gram-positive bacterium comprising an expression cassette according to claim 1.

16. An expression cassette comprising,
a polynucleotide encoding luciferase luxA, luxB, and eukaryotic luc gene products, wherein (a) transcription of the polynucleotide results in a polycistronic RNA encoding all three gene products, (b) polynucleotide sequences comprising Gram-positive ribosome-binding site sequences are located adjacent the 5' end of the luxA coding sequences, adjacent the 5' end of the luxB coding sequences, and adjacent the 5' end of the luc coding sequences, and (c) each of the luxA, luxB, and luc gene products is expressed as an individual polypeptide.

17. The expression cassette of claim 16, wherein said polynucleotide further encodes luxC, luxD and luxE gene products, wherein (i) Gram-positive ribosome-binding site sequences are located 5' to each of the luxC, luxD, and luxE coding sequences, and (ii) each of the luxC, luxD, and luxE gene products is expressed as an individual polypeptide and further wherein the lux gene products are obtained from bacteria having a naturally occurring lux operon ordered luxCDABE—after "polypeptide".

18. The expression cassette of claim 17, further comprising a multiple-insertion site located 5' to said luxA, luxB, luc, luxC, luxD and luxE coding sequences.

19. The expression cassette of claim 17, wherein the arrangement of the coding sequences for the lux gene products is in the following relative order 5'-luxA-luxB-luxC-luxD-luxE-3'.

20. The expression cassette of claim 16, wherein the polynucleotide further comprises a promoter located 5' to all of said lux and luc coding sequences wherein transcription of the polynucleotide results in a polycistronic RNA encoding all the lux and luc gene products.

21. The expression cassette of claim 20, wherein said promoter is contained in an Expression Enhancing Sequence selected from the group consisting of Sa1 (SEQ ID NO:15), Sa2 (SEQ ID NO:16), Sa3 (SEQ ID NO:17), Sa4 (SEQ ID NO:18), Sa5 (SEQ ID NO:19), and Sa6 (SEQ ID NO:20).

22. The expression cassette of claim 20, wherein said promoter is contained in an Expression Enhancing Sequence selected from the group consisting of Sp1 (SEQ ID NO:21), Sp5 (SEQ ID NO:22), Sp6 (SEQ ID NO:23), Sp9 (SEQ ID NO:24), Sp16 (SEQ ID NO:25) and Sp17 (SEQ ID NO:26).

23. The expression cassette of claim 22, wherein said promoter is contained in Expression Enhancing Sequence Sp16 (SEQ ID NO:25).

24. The expression cassette of claim 16, wherein the coding sequences for luxA and luxB are obtained from *Photorhabdus luminescens*.

25. The expression cassette of claim 16, wherein the expression cassette is contained within a bacterial transposon.

26. The expression cassette of claim 16, wherein the expression cassette is contained within a bacterial mini-transposon.

27. The expression cassette of claim 16, wherein the coding sequences of the gene products comprise codons that are optimal for expression of the gene products in a host system into which the expression cassette is to be introduced.

28. A shuttle vector comprising:
an expression cassette according to claim 16;
a polynucleotide encoding a selectable marker;
a Gram-positive origin of replication; and
a Gram-negative origin of replication.

29. A Gram-positive bacterium comprising an expression cassette according to claim 16.

30. A bacterium comprising the vector of claim 12.

31. A bacterium comprising the vector of claim 28.

32. A method of modifying a Gram-positive bacterium to produce light, comprising transforming the Gram-positive organism with an expression cassette according to claim 16.

33. The method of claim 32 further comprising providing the substrate required for luc-mediated luciferase activity.

34. A method of screening an analyte for its ability to affect expression of a reporter marker, comprising:
providing the analyte to Gram-positive bacteria comprising the luciferase expression cassette of claim 16, wherein said reporter marker comprises luciferase;
providing a substrate required for luciferase light production; and
monitoring the effect of the analyte on the ability of the Gram-positive bacteria to produce light, thereby identifying whether the analyte affects expression of the reporter in Gram-positive bacteria.

35. The method of claim 34, wherein said substrate comprises an aldehyde, and said aldehyde is provided as a vapor.

36. The method of claim 34, wherein said substrate is a substrate for the luc gene product.

37. The method of claim 34, wherein said substrate comprises (i) an aldehyde, wherein said aldehyde is provided as a vapor, and (ii) a substrate for the luc gene product.

* * * * *

SEQUENCE LISTING

<160> NUMBER OF SEQ ID NOS: 26

<210> SEQ ID NO 1
<211> LENGTH: 6
<212> TYPE: DNA
<213> ORGANISM: Artificial Sequence
<220> FEATURE:
<223> OTHER INFORMATION: Description of Artificial Sequence:
      Gram-positive ribosome binding site

<400> SEQUENCE: 1 aggagg                                                                  6

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Primer
      XAF3

<400> SEQUENCE: 2
ccccggatcc tgcagatgaa gcaagaggag gactctctat g                           41

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Primer XAR

<400> SEQUENCE: 3
ggcggatccg tcgacttaat ataatagcga acgttg          36

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Primer XBF

<400> SEQUENCE: 4
gggaattctc gaggaggaga gaaagaaatg aaatttgga          39

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Primer XBR

<400> SEQUENCE: 5
ggcggatccg tcgacttagg tatattccat gtggtac          37

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence: Primer XCF

<400> SEQUENCE: 6
gggaattctc gaggaggatg gcaaatatga ctaa          34

<210> SEQ ID NO 7
<211> LENGTH: 37
<212> TYPE: DNA
<213> ORGANISM: Artificial Sequence
<220> FEATURE:
<223> OTHER INFORMATION: Description of Artificial Sequence: Primer XCR

<400> SEQUENCE: 7
ggcggatccg tcgacttatg ggacaaatac aaggaac          37

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Primer XDF

<400> SEQUENCE: 8
gggaattctc gaggaggagt aaaagtatgg aaaatga          37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial Sequence: Primer XDR

<400> SEQUENCE: 9
ggcggatccg tcgacttaag acagagaaat tgcttga          37

<210> SEQ ID NO 10

<210> SEQ ID NO 10
<211> LENGTH: 39
<212> TYPE: DNA
<213> ORGANISM: Artificial Sequence
<220> FEATURE:
<223> OTHER INFORMATION: Description of Artificial Sequence: Primer XEF

<400> SEQUENCE: 10
gggaattctc gaggaggaaa acaggtatga cttcatatg        39

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Primer XER

<400> SEQUENCE: 11
ggcggatccg tcgacttaac tatcaaacgc ttcggtta         38

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: LUXA-REV

<400> SEQUENCE: 12
ccacactcct cagagatgcg                             20

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: BamH I
      recognition sequence

<400> SEQUENCE: 13 ggatcc                                            6

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: vector
      sequence

<400> SEQUENCE: 14
ggatcctgca gatgaagcaa gaggaggact ctctatg          37

<210> SEQ ID NO 15
<211> LENGTH: 645
<212> TYPE: DNA
<213> ORGANISM: Artificial Sequence
<220> FEATURE:
<223> OTHER INFORMATION: Description of Artificial Sequence: pMK4
      luxABCDE Sa1

<400> SEQUENCE: 15
atttatctaa agatgagatt aagccaatag aacgtcatta gcaaaataaa ttatattgcg    60
tcctacaagc aagttcatgc ttatgtttgt aggggggttat tgtggagaat aaaattattt   120
ccaatagaga agggatggta atcattttat agtgaaatat tatgaaattg taataattta   180
gatattgtaa aatctaataa gttgtaataa ttttaagggg taattataaa atttgatgat   240

-continued

```
acagtatatg attttttttgt aatcataatg tcatcaaaca tcaacctatt atacataata      300
aaatcgtata atgatgtagt attcataaat tcggataaaa gaatgttagg aaagttaagc      360
aagaggagga ttttaaagtg caaaaaaaga taattgcagc tattattggg caagcgcga       420 ttagcgctgt tgcggcaact caagcaaatg cggctacaac tcacacagta aaaccgggtg     480
aatcagtgtg ggcaatttca ataagtatg ggatttcgat tgctaaatta aagtcattaa       540
acaatttaac atctaatcta atttcccaa accaagtact aaaagtatct ggctcaagta       600
attctacgag taatagtagc cgtccatcaa cgaactcagg tggcg                      645
```

<210> SEQ ID NO 16
<211> LENGTH: 671
<212> TYPE: DNA
<213> ORGANISM: Artificial Sequence
<220> FEATURE:
<221> NAME/KEY: base_polymorphism
<222> LOCATION: 26
<223> OTHER INFORMATION: /note = "'n' represents an a or g or t or c polymorphism at this position
<221> NAME/KEY: base_polymorphism
<222> LOCATION: 79
<223> OTHER INFORMATION: /note = "'n' represents an a or g or t or c polymorphism at this position
<223> OTHER INFORMATION: Description of Artificial Sequence: pMK4 luxABCDE Sa2

<400> SEQUENCE: 16

```
aaaaaatgag gggtgagacg tgaaantaaa gaaagataac gtagagaagc aatcagccac      60
caaattgata gcaatcccnt tcatcacaga ccatgaacta agcgacttat ttcaaagtga     120
gtatacaaac aattcgttta gatcgcactt atttaaacat accagaatta agaagcgtat    180
taaattagtt gctgaaaaga attatgacca ataagttct attgaagaac aagaatttat     240
tggtgatttg attcaagtca atccaaatgt taaagcgcaa tcaattttag atattacatc    300
ggattctgtt tttcataaaa ctggaattgc gcgtggtcat gtgctgtttg ctcaggcaaa    360
ttcgttatgt gttgcgctaa ttaagcaacc aacagtttta actcatgaga gtagcattca    420
atttattgaa aaagtaaaat taaatgatac ggtaagagca gaagcacgag ttgtaaatca    480
aactgcaaaa cattattacg tcgaagtaaa gtcatatgtt aaacatacat tagttttcaa    540
aggaaatttt aaaatgtttt atgataagcg aggataaaat tatggttaaa ttagcaattg    600
atatgatggg tggcgacaat gcgcctgata tcgtattaga agccgtacaa aaggctgttg    660
aagactttaa a                                                          671
```

<210> SEQ ID NO 17
<211> LENGTH: 623
<212> TYPE: DNA
<213> ORGANISM: Artificial Sequence
<220> FEATURE:
<221> NAME/KEY: base_polymorphism
<222> LOCATION: 19
<223> OTHER INFORMATION: /note = "'n' represents an a or g or t or c polymorphism at this position
<221> NAME/KEY: base_polymorphism
<222> LOCATION: 32
<223> OTHER INFORMATION: /note = "'n' represents an a or g or t or c polymorphism at this position
<221> NAME/KEY: base_polymorphism
<222> LOCATION: 37
<223> OTHER INFORMATION: /note = "'n' represents an a or g or t or c polymorphism at this position
<221> NAME/KEY: base_polymorphism
<222> LOCATION: 48
<223> OTHER INFORMATION: /note = "'n' represents an a or g or t or c polymorphism at this position

```
<221> NAME/KEY: base_polymorphism
<222> LOCATION: 85
<223> OTHER INFORMATION: /note = "'n' represents an a or g or t or c
      polymorphism at this position
<221> NAME/KEY: base_polymorphism
<222> LOCATION: 103
<223> OTHER INFORMATION: /note = "'n' represents an a or g or t or c
      polymorphism at this position
<221> NAME/KEY: base_polymorphism
<222> LOCATION: 154
<223> OTHER INFORMATION: /note = "'n' represents an a or g or t or c
      polymorphism at this position
<223> OTHER INFORMATION: Description of Artificial Sequence: pMK4
      luxABCDE Sa3

<400> SEQUENCE: 17
gatgggtaag aagaaaatnc ggcatcaggg gncattngcc attcaggntg ggaactgttg      60
gaagggcgtc gggcggcctt ttcgntattc gcagctgcga aangggatgt gctgaaggcg     120
attaagttgg gtaacgccag ggtttcccag tcangcgttg taaacggcgg ccagtgaatt     180
cccggggatc aagccgttta agtattacga ccagtttata tcattcatgg taaaggacag    240
ggccttcaaa aaggtgtaca acaacatttg aaaagcataa agtgttagtg acttagaggt    300
ggtatgccaa ggaaggtgga tttggcgtta ccgttgcaac actaaaataa attataattt    360
gataaattaa atagctgcag ttaaaataat gtaaagcaac aagaatacat ttcaaacatg    420
ttatttgaaa taagcataaa aattgagcaa atagaaatac atgaagcatg ttatctgata    480
taatttgaac atcataataa taattaagga ggattggcat ttatggcaat cgtaaaagta    540
acagatgcag attttgattc aaaagtagaa tctggtgtac aactagtaga tttttgggca    600
acatggtgtg gtccatgtaa aat                                             623

<210> SEQ ID NO 18
<211> LENGTH: 671
<212> TYPE: DNA
<213> ORGANISM: Artificial Sequence
<220> FEATURE:
<221> NAME/KEY: base_polymorphism
<222> LOCATION: 249
<223> OTHER INFORMATION: /note = "'n' represents an a or g or t or c
      polymorphism at this position
<223> OTHER INFORMATION: Description of Artificial Sequence: pMK4
      luxABCDE Sa4

<400> SEQUENCE: 18
gatgtatatt cacggggcac atgctgccga aaagcatcac cattaggtgc aatgtcatta      60
ctattgggac ggtttttata ttttattgct actcaaggtt ttgtaaatat gcaattaatc    120
ggtgcgatta tctttgtatt aattacaggt cctcttttca agtcatatga ttatgaaagc    180
agcatataat attaaaacgc cttatactaa aaagactaaa gcgatgaaat ttcggaagac    240
ttaaaagcnc aaaattgtag attatataac aaaatcatga atataaatca acaacaaaca    300
gcagtaagat gattccaaat taggaatgat tttactgctg ttttcttttg acattgttac    360
ctctttttca atgatttttt ctttgactac agattcgccc tatctacata tatctcttta    420
atttaattgc ctttcatgtc gttatgtatt atgataataa taattataaa tcgtaacgat    480
tacgttttaa aaagagagag gttttattat gcattggaca attatcggcg gtggcataca    540
gggaactgca atcgcacaaa aactattatc aagcggatta acaacagacc gattaacaat    600
cattgaccca cacgaaactt tttgccaaag gtttaactca tatacaaatc gaatagaaat    660
gccttatttt a                                                          671
```

<210> SEQ ID NO 19
<211> LENGTH: 650
<212> TYPE: DNA
<213> ORGANISM: Artificial Sequence
<220> FEATURE:
<221> NAME/KEY: base_polymorphism
<222> LOCATION: 1
<223> OTHER INFORMATION: /note = "'n' represents an a or g or t or c polymorphism at this position
<221> NAME/KEY: base_polymorphism
<222> LOCATION: 7
<223> OTHER INFORMATION: /note = "'n' represents an a or g or t or c polymorphism at this position
<221> NAME/KEY: base_polymorphism
<222> LOCATION: 8
<223> OTHER INFORMATION: /note = "'n' represents an a or g or t or c polymorphism at this position
<221> NAME/KEY: base_polymorphism
<222> LOCATION: 34
<223> OTHER INFORMATION: /note = "'n' represents an a or g or t or c polymorphism at this position
<221> NAME/KEY: base_polymorphism
<222> LOCATION: 113
<223> OTHER INFORMATION: /note = "'n' represents an a or g or t or c polymorphism at this position
<221> NAME/KEY: base_polymorphism
<222> LOCATION: 118
<223> OTHER INFORMATION: /note = "'n' represents an a or g or t or c polymorphism at this position
<223> OTHER INFORMATION: Description of Artificial Sequence: pMK4 luxABCDE Sa5

<400> SEQUENCE: 19
naccagnnaa aatggtaata aaaatggcag aagnaataaa aaaaggataa agagatccca      60
aacggtatag agcttagtat aaaattttcg gacaataaaa taaatacggg ttnaaccnaa     120
ttttaacggg aaagcacttc agaatatggt gtgtttgatc aagaataaaa ttaatgatga     180
aaatttaacg gagaatagtg tatattgagt agatcaagaa taaaaagata attctactat     240
tgttgtgaag gcaaataagt agaagatttt aagtgtaatt tctggtgatt taaataataa     300
tataaatgga agtactgata taaaactttt taacctacta gattcttata atttgctttc     360
cattttatga cgatttttac tcaattgagt gatagaatca aaaaagccat ctcaaaaatt     420
aatcaagcaa acaacattcc aaacaatgct cgcaaatcac caatgtatca ctctccaatt     480
acgtaactat gatttaattt aagcatagtt attgaggttt tgtgatatat agtataaaat     540
taatgagaat taaatttaat aatgtaaaat tcatcttcgg ggtcgggtgt aattcccaac     600
cggcagtaaa taaagcctgc gacctgctag tatgtatcat attagtggct                650

<210> SEQ ID NO 20
<211> LENGTH: 677
<212> TYPE: DNA
<213> ORGANISM: Artificial Sequence
<220> FEATURE:
<221> NAME/KEY: base_polymorphism
<222> LOCATION: 19
<223> OTHER INFORMATION: /note = "'n' represents an a or g or t or c polymorphism at this position
<221> NAME/KEY: base_polymorphism
<222> LOCATION: 66
<223> OTHER INFORMATION: /note = "'n' represents an a or g or t or c polymorphism at this position
<221> NAME/KEY: base_polymorphism
<222> LOCATION: 97
<223> OTHER INFORMATION: /note = "'n' represents an a or g or t or c polymorphism at this position
<221> NAME/KEY: base_polymorphism
<222> LOCATION: 99
<223> OTHER INFORMATION: /note = "'n' represents an a or g or t or c polymorphism at this position
<221> NAME/KEY: base_polymorphism
<222> LOCATION: 119
<223> OTHER INFORMATION: /note = "'n' represents an a or g or t or c polymorphism at this position
<223> OTHER INFORMATION: Description of Artificial Sequence: pMK4 luxABCDE Sa6

<400> SEQUENCE: 20

```
cggaagaacg ctttgaagnt taagctaatt acatctcatc atatgcacgg agatccttaa      60
atgccnaatt gaaagatatt tatatgaatc atcgagncng tcttgatgta gctattgcna     120
gcagatgata tttgtccagc aataactaat ggggaacaag tgaaaggcct ttacctttat     180
ggtccatttg ggcaggtaaa tcttttattc taggtgcaat tgcggaatca gctcaaatct     240
aagaaggtac gttcgacaat tatttattta ccgggaattt attagaacat taaaaggtgg     300
ctttaaagat ggttcttttg aaaagaaatt acatcgcgta agagaagcaa acattttaat     360
gcttgatgat attggggctg aagaagtgac tccatgggtg agagatgagg taattggacc     420
tttgctacat tatcgaatgg ttcatgaatt accaacattc tttagttcta attttgacta     480
tagtgaattg gaacatcatt tagcgatgac tcgtgatggt gaagaagaa  ctaaagcagc     540
acgtattatt gaacgtgtca atctttgtc  aacaccatac tttttatcag gagaaaattt     600
cagaaacaat tgaattttaa aatgattggt gtataatgaa tacaaatcta atcgtttaa      660
atgattgaag acaagat                                                    677
```

<210> SEQ ID NO 21
<211> LENGTH: 622
<212> TYPE: DNA
<213> ORGANISM: Artificial Sequence
<220> FEATURE:
<221> NAME/KEY: base_polymorphism
<222> LOCATION: 7
<223> OTHER INFORMATION: /note = "'n' represents an a or g or t or c polymorphism at this position
<221> NAME/KEY: base_polymorphism
<222> LOCATION: 33
<223> OTHER INFORMATION: /note = "'n' represents an a or g or t or c polymorphism at this position
<221> NAME/KEY: base_polymorphism
<222> LOCATION: 97
<223> OTHER INFORMATION: /note = "'n' represents an a or g or t or c polymorphism at this position
<221> NAME/KEY: base_polymorphism
<222> LOCATION: 126
<223> OTHER INFORMATION: /note = "'n' represents an a or g or t or c polymorphism at this position
<223> OTHER INFORMATION: Description of Artificial Sequence: pDL289 luxABCDE Sp1

<400> SEQUENCE: 21

```
aggacgntag gacgtgacga gccgaaaggc ttnagcgttc gagccgacac ggacaaagga      60
cgccgccctt ggttacttgt tgtcaattag accatgnaat aaagtaagcg gacatggtat     120
aatagntagg tcgcaacgtt ctttcgctaa gttacgaact tagattggag gtgagcgccc     180
aatacgcaaa ccgcctctcc ccgcgcgttg ccgattcatt aatgcagctg gcacgacagg     240
tttcccgact ggaaagcggg cagtgagcgc aacgcaatta atgtgagtta gctcactcat     300
taggcacccc aggctttaca ctttatgctt ccggctcgta tgttgtgtgg aattgtgagc     360
ggataacaat ttcacacagg aaacagctat gaccatgatt acgccaagct atttaggtga     420
cactatagaa tactcaagct atgcatccaa cgcgttggga gctctccgga tcaggtcatt     480
cgagttaccg atttatcaca tagatgatat ggtaagattc agttagaaga aagagtcaca     540
aacacacttt gtggcttttt tatttccata aaaatggtaa aatagtagga gtagaaatgg     600
```

| agttcgagac atgaaagtaa ta | 622 |

<210> SEQ ID NO 22
<211> LENGTH: 610
<212> TYPE: DNA
<213> ORGANISM: Artificial Sequence
<220> FEATURE:
<221> NAME/KEY: base_polymorphism
<222> LOCATION: 119
<223> OTHER INFORMATION: /note = "'n' represents an a or g or t or c polymorphism at this position
<223> OTHER INFORMATION: Description of Artificial Sequence: pDL289 luxABCDE Sp5

<400> SEQUENCE: 22

| agacaaagaa cgtccgccct tggtacttgt tgtcaaatta gaccatggaa taaagtaagc | 60 |
| ggacatggta taatagctag gtcgcaacgt tctttcgcta agttacgaac ttagattgna | 120 |
| ggtgagcgcc caatacgcaa accgcctctc cccgcgcgtt ggccgattca ttaatgcagc | 180 |
| tggcacgaca ggtttcccga ctggaaagcg ggcagtgagc gcaacgcaat taatgtgagt | 240 |
| tagctcactc attaggcacc ccaggcttta cactttatgc ttccggctcg tatgttgtgt | 300 |
| ggaattgtga gcggataaca atttcacaca ggaaacagct atgaccatga ttacgccaag | 360 |
| ctatttaggt gacactatag aatactcaag ctatgcatcc aacgcgttgg gagctctccg | 420 |
| gatcgtctgc caggttcagc aacacgccca catccgggcg caagtggctg gaccaatgca | 480 |
| actggaaaga agagagctcg gcgcagagaa cgtcgaggcg aggggtggcc gtgagggcgt | 540 |
| cgaaaagcga aacgccgata ttgcccaccg ccagtgcgcg cttgccggtg cgcttggcat | 600 |
| ctgcctgcat | 610 |

<210> SEQ ID NO 23
<211> LENGTH: 626
<212> TYPE: DNA
<213> ORGANISM: Artificial Sequence
<220> FEATURE:
<221> NAME/KEY: base_polymorphism
<222> LOCATION: 12
<223> OTHER INFORMATION: /note = "'n' represents an a or g or t or c polymorphism at this position
<223> OTHER INFORMATION: Description of Artificial Sequence: pDL289 luxABCDE Sp6

<400> SEQUENCE: 23

| atgcttccgg gntcgtatgt tgtgtggaat tgtgagcgga ataccaattt cacacaggaa | 60 |
| acagctatga ccatgattac gccaagctta tttaggtgac actatagaat actcaagcta | 120 |
| tgcatccaac gcgttgggag ctctccggat caaaatgaca atcggcagca tgtgcgggat | 180 |
| ggattatgcg agtcggacat cttgcctagg acgcgcccca actgggagca gcccttcatc | 240 |
| aaggagtaca gcaaatcatt gccgctgcgc ggcatgaact cgtgggcttc aaagcttgcc | 300 |
| cacatcttct tgcgggcaaa gataccggca ataccgagga tgaggaccac tagcgagata | 360 |
| aggaaaggaa cgttgagccc gtgccagagg gcaaggtgcg aatgatgctc aatcccacg | 420 |
| gcagccactg catcatcgat cggggcatca agagcccga gcacaaatac cagcggcaga | 480 |
| gacataaagc ccggcaaagc tgcaggtagc cacagcgaca ctggtgcttc atggacatct | 540 |
| cccatgtcgc gaggtccgtc aaagaaggcg ccgaagacaa tctttgcgga gtaagtaaag | 600 |
| gtgaagaacg caccgatacc ggcaac | 626 |

<210> SEQ ID NO 24
<211> LENGTH: 607

```
<212> TYPE: DNA
<213> ORGANISM: Artificial Sequence
<220> FEATURE:
<223> OTHER INFORMATION: Description of Artificial Sequence: pDL289
      luxABCDE Sp9

<400> SEQUENCE: 24
gcaaggcctt gagtagcttt atccagactg aaggcccgct atctttggaa ggcaggatat     60
aaaagaagat tctgttgcag agcgggcgga acgagtaggc tatgtgctgc aaaatcccaa    120
tcaaatgatt tcaaccaata tgattttga  tgaggtggct ctgggactcc gtttgcgagg    180
tgtggacgag caggaaattg aaacgagagt ctatgaaacc ttgaaaatct gtggtctcta    240
tgaattccgt aattggccca tttctgccct gtcatttggt cagaaaaaac gtgtgactat    300
tgcctcaatt ttggtcttag gcgctgaaat tatcctccta gatgaaccga ctgcgggtca    360
agaccagaag aactatactg agattatgga atttctcgaa gaactgcatc aacaagggca    420
taccattgtc atgattaccc atgatatgca attgatgctg gattattcag atcgagccct    480
tgtcatggtg gatggggaat tgattgctga tactgatcca gctagtctgt tgagcaatcc    540
tgagctgtta gtaaaagcca acctaaaaga gacttctatc ttcaacttgg ctaagaaact    600
cgacgtg                                                              607

<210> SEQ ID NO 25
<211> LENGTH: 616
<212> TYPE: DNA
<213> ORGANISM: Artificial Sequence
<220> FEATURE:
<221> NAME/KEY: base_polymorphism
<222> LOCATION: 91
<223> OTHER INFORMATION: /note = "'n' represents an a or g or t or c
      polymorphism at this position
<223> OTHER INFORMATION: Description of Artificial Sequence: pDL289
      luxABCDE Sp16

<400> SEQUENCE: 25
tgaatgttcg gtacgcacca gtcttcgtct gctctcaagg acgtggacat tcatgatgga     60
tttgccacta cgaagatgac ctaagtcagt ncaagaagaa attattaaga aaaataaagg    120
tgaagactta atccgtcctc actctagaag gaagtcactt agtggcttcc ttttgtcttt    180
agaaaatacc tctaaatatg gtaaaatagt agaagaataa tgtgaggaaa atgaatgtca    240
aatagttttg aaattttgat gaatcaattg gggatgcctg ctgaaatgag acaggctcct    300
gctttagcac aggccaatat tgagcgagtt gtggttcata aaattagtaa ggtatgggag    360
tttcatttcg tattttctaa tattttaccg attgaaatct ttttagaatt aaagaaaggt    420
ttgagcgaag aattttctaa gacaggcaat aaagctgttt ttgaaattaa ggctcggtct    480
caagaatttt caaatcagct cttgcagtcc tactataggg aggctttctc tgaaggtcca    540
tgtgctagtc aaggttttaa gtccctttat caaaatttgc aagttcgtgc tgagggtaat    600 cagctatttta ttgaag                                                   616

<210> SEQ ID NO 26
<211> LENGTH: 609
<212> TYPE: DNA
<213> ORGANISM: Artificial Sequence
<220> FEATURE:
<221> NAME/KEY: base_polymorphism
<222> LOCATION: 36
<223> OTHER INFORMATION: /note = "'n' represents an a or g or t or c
      polymorphism at this position
<221> NAME/KEY: base_polymorphism
<222> LOCATION: 76
```

-continued

```
<223> OTHER INFORMATION: /note = "'n' represents an a or g or t or c
      polymorphism at this position
<223> OTHER INFORMATION: Description of Artificial Sequence: pDL289
      luxABCDE Sp17

<400> SEQUENCE: 26
tgaaaaagca gggctatgtg aagcgctggc gccgancccc gatgatgagc gtcgcaccct      60
cgctgccctg actgcngacg gcgcctccct ccgcacccgc gccgaatgca tccccgaagc     120
catggccaag gcctataagg aggtaggcct cgaccttgcc gagttcaaga aatcgctgac     180
atcctggccg gcgtgcctgt ggacgtggag ctgccgtggc catctgggga tgactttgtg     240
ggttaaagtg tggccttcat atagcagatg aggacggcta tactggctta agagttttga     300
ctctatttac gtaaaatttt ttcacactat gagaggaggg gccatggcta cagcagtaga     360
cgtcgcgcag gttatctaca acaaactggg gtgggtcgat gcgtggaagc tggagaagct     420
tacgtattac tgccaagcgt ggagcctggg ctggtacggg cgacctcttg tctcgaatga     480
atttcaggcg tggaaggacg gtccggttga acccgacctc tatcgcgaga ataaatatca     540
acgctccgaa aaatcctcca cggtgttacc gggagctgat gtagaggcta taggggagga     600
agccgaaaa                                                             609
```